United States Patent
Ma et al.

(10) Patent No.: US 11,065,239 B2
(45) Date of Patent: Jul. 20, 2021

(54) USE OF EZH2 INHIBITOR COMBINED WITH BTK INHIBITOR IN PREPARING DRUG FOR TREATING TUMOR

(71) Applicant: Jiangsu Hengrui Medicine Co., Ltd., Jiangsu (CN)

(72) Inventors: Ke Ma, Jiangsu (CN); Guoqing Cao, Jiangsu (CN); Changyong Yang, Jiangsu (CN); Lianshan Zhang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 79 days.

(21) Appl. No.: 16/611,969

(22) PCT Filed: May 17, 2018

(86) PCT No.: PCT/CN2018/087246
§ 371 (c)(1),
(2) Date: Nov. 8, 2019

(87) PCT Pub. No.: WO2018/210296
PCT Pub. Date: Nov. 22, 2018

(65) Prior Publication Data
US 2021/0030736 A1 Feb. 4, 2021

(30) Foreign Application Priority Data
May 18, 2017 (CN) .......................... 201710350614.6

(51) Int. Cl.
*A61K 31/4545* (2006.01)
*A61P 35/04* (2006.01)
*A61K 31/5025* (2006.01)
*A61K 45/06* (2006.01)

(52) U.S. Cl.
CPC ...... *A61K 31/4545* (2013.01); *A61K 31/5025* (2013.01); *A61P 35/04* (2018.01); *A61K 45/06* (2013.01)

(58) Field of Classification Search
None
See application file for complete search history.

(56) References Cited

U.S. PATENT DOCUMENTS

| 10,759,787 B2* | 9/2020 | Lu ....................... A61K 31/4545 |
| 2015/0065483 A1 | 3/2015 | Kuntz et al. |
| 2016/0022684 A1* | 1/2016 | Kuo ....................... A61K 45/06 424/133.1 |

FOREIGN PATENT DOCUMENTS

| CN | 105263496 A | 1/2016 |
| WO | 2013/049770 A2 | 4/2013 |
| WO | 2013/067300 A1 | 5/2013 |
| WO | 2014/097041 A1 | 6/2014 |
| WO | 2014/166820 A1 | 10/2014 |
| WO | 2014/168975 A1 | 10/2014 |
| WO | 2015/146159 A1 | 10/2015 |
| WO | 2016/007185 A1 | 1/2016 |
| WO | 2017/084494 A1 | 5/2017 |

OTHER PUBLICATIONS

Int'l Search Report dated Aug. 1, 2018 in Int'l Application No. PCT/CN2018/087246.
Schultz et al, "Asymmetric Synthesis of 1,6-Dialkyl-1,4-cyclohexadine Derivatives," Journal of the American Chemical Society, vol. 113, No. 13, pp. 4931-1936 (1991).
Extended European Search Report dated Feb. 4, 2021 in corresponding EP Application No. 18802340.2.
Biao Lu, et al., "Discovery of EBI-2511: A Highly Potent and Orally Active EZH2 Inhibitor for the Treatment of Non-Hodgkin's Lymphoma," ACS Medicinal Chemistry Letters, vol. 9, No. 2, pp. 98-102, Feb. 8, 2018.

* cited by examiner

*Primary Examiner* — Brian J Davis
(74) *Attorney, Agent, or Firm* — Ice Miller LLP

(57) ABSTRACT

This application describes a use of an EZH2 inhibitor combined with a BTK inhibitor in preparing a drug for treating a tumor is described.

20 Claims, 3 Drawing Sheets

USE OF EZH2 INHIBITOR COMBINED WITH BTK INHIBITOR IN PREPARING DRUG FOR TREATING TUMOR

CROSS REFERENCE TO RELATED APPLICATION

This application is a Section 371 of International Application No. PCT/CN2018/087246, filed May 17, 2018, which was published in the Chinese language on Nov. 22, 2018, under International Publication No. WO 2018/210296 A1, which claims priority under 35 U.S.C. § 119(b) to Chinese Application No. 201710350614.6, filed May 18, 2017, the disclosures of which are incorporated herein by reference in their entirety.

FIELD OF THE INVENTION

The present invention relates to a combination of an EZH2 inhibitor and a BTK inhibitor, as well as a use thereof in the preparation of a medicament for treating tumors.

BACKGROUND OF THE INVENTION

Lymphoma is a lymphoid malignancy that originates in the lymph nodes and/or extranodal lymphoid tissues. According to the presence of Reed-Sternberg cells (R—S cells) in pathology, lymphoma can be classified into Hodgkin Lymphoma (HL) and Non-Hodgkin Lymphoma (NHL). In 2015, the incidence of malignant lymphoma in China was 8.82/100,000, ranking the eleventh in the incidences of all kinds of tumors. The incidence of malignant lymphoma in male is higher than that in female, and they are 5.30/100,000 and 3.52/100,000, respectively. In 2015, the mortality rate of malignant lymphoma in China was 5.21/100,000, ranking the $10^{th}$ among the tumor death cases.

In Asia, 90% of lymphoma patients are NHL patients having lymphocytes, histiocytes or reticular cells with different degrees of differentiation in pathology. According to the natural course of NHL, NHL can be classified into three major clinical types, namely highly invasive, invasive and indolent lymphoma. According to the different lymphocyte origins, it can be classified into B cells, T cells and natural killer (NK) cells lymphoma. The main function of B cells is to secrete various antibodies to protect the body against various external invasions.

The histone methyltransferase encoded by the EZH2 gene is the catalytic component of polycomb repressive complex 2 (PRC2). EZH2 levels are abnormally elevated in cancer tissues compared to normal tissues, and EZH2 is most highly expressed in advanced tumors or poor prognosis. In some types of tumors, EZH2 overexpression occurs simultaneously with amplification of the EZH2 gene. A number of si/shRNA experimental studies show that reduction of EZH2 expression in tumor cell lines can inhibit tumor cell proliferation, migration and invasion, or angiogenesis, and lead to apoptosis. WO2017084494 (PCT/CN2016/104318, filing date of 2 Nov. 2016) discloses an EZH2 inhibitor having the following structure:

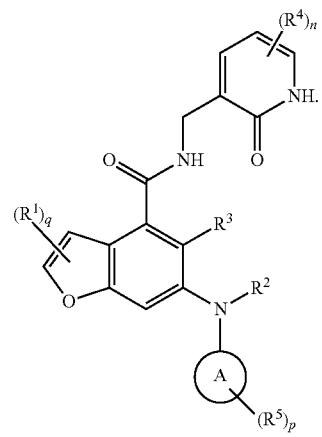

Bruton's tyrosine kinase (BTK) is a member of tyrosine kinase subfamily, and belongs to the Tec family of kinases. It is mainly expressed in B cells, and distributed in the lymphatic system, hematopoietic and hematological systems. B cell receptor (BCR) plays a crucial role in regulating the proliferation and survival of various lymphomas including the subtypes of chronic lymphocytic leukemia (CLL) and non-Hodgkin lymphoma (NHL), mantle cell lymphoma (MCL), and diffuse large B-cell lymphoma (DLBCL). In addition, the effects of B cells in the pathogenesis of rheumatoid arthritis, systemic lupus erythematosus, multiple sclerosis, and other immune diseases have been proven in clinical practice. Bruton's tyrosine kinase (BTK) is a key protein kinase in the BCR signaling pathway. It can regulate the maturation and differentiation of normal B cells, and is also closely related to various diseases of B cell lymphoid tissue disorders. Therefore, small molecule inhibitors targeting BTK can be beneficial to the treatment of B cell malignancies and autoimmune diseases. WO2016007185A1 (publication date of 14 Jan. 2014) discloses a BTK inhibitor having the following structure:

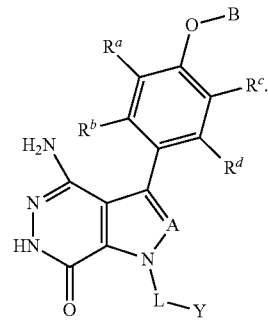

B cells located in the germinal center are called germinal center B cells (GC B cells). GC B cells divide very rapidly and mange to produce high-affinity antibodies that help against invasive infections, and the remaining GC B cells are apoptotic. Due to the rapid division of GC B cells and simultaneous VW rearrangement, the DNA repair is attenuated. Therefore, the germinal center is the engine of lymphoma formation. Unfortunately, when this happens, many other genes also are mutated, which eventually lead to the formation of lymphoma, such as germinal center B cell-like diffuse large B-cell lymphoma and follicular lymphoma.

B cell lymphoma derived from germinal center has been shown to have persistent activation of BTK and EZH2 mutations (Y641, Y646, A682, A692 and the like) or overexpression. The combination of a BTK inhibitor and an EZH2 inhibitor can simultaneously inhibit tumor cell proliferation caused by abnormal (or excessive) activation of BTK and EZH2 mutation (or overexpression), resulting in a synergistic anti-tumor effect.

Patent applications WO2014168975A1 (publication date of 16 Oct. 2014), WO2014166820A1 (publication date of 16 Oct. 2014) and WO2015146159A1 (publication date of 1 Oct. 2015) disclose combinations of an EZH2 inhibitor and a BTK inhibitor in treating B cell proliferative diseases. The present invention provides a use of a combination of an EZH2 inhibitor and a BTK inhibitor in the preparation of a medicament for treating tumors, wherein the EZH2 inhibitor and BTK inhibitor have novel structures and the combination has a synergistic effect.

SUMMARY OF THE INVENTION

The technical problem to be solved by the present invention is to provide a use of a combination of an EZH2 inhibitor and a BTK inhibitor in the preparation of a medicament for treating tumors, wherein the combination has a synergistic effect.

The technical solutions of the present invention are as follows:

The present invention provides a use of a combination of an EZH2 inhibitor and a BTK inhibitor in the preparation of a medicament for treating tumors, characterized in that the EZH2 inhibitor is a compound of formula (I)

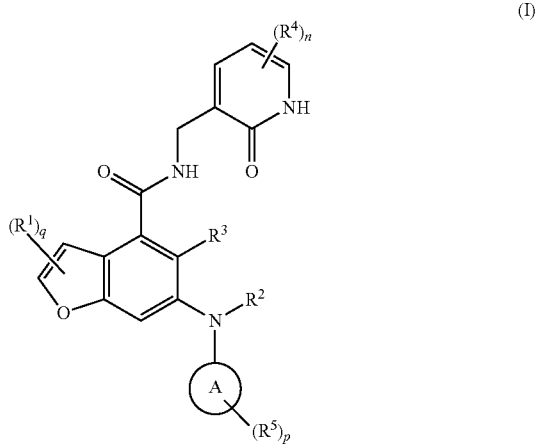

or a pharmaceutically acceptable salt thereof or a stereoisomer thereof, wherein, ring A is selected from the group consisting of heterocyclyl and cycloalkyl;

each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$(CH_2)_xR^a$, wherein the alkyl, haloalkyl, heterocyclyl, aryl and heteroaryl are each independently and optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —$NR^7R^8$, wherein the cycloalkyl and heterocyclyl are each independently and optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^2$ is hydrogen or alkyl, wherein the alkyl is optionally substituted by one or more substituents selected from the group consisting of halogen, hydroxy, cyano, cycloalkyl and heterocyclyl;

$R^3$ is selected from the group consisting of hydrogen, alkyl, halogen, cyano, alkoxy and haloalkyl;

each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$C(O)R^6$, —$C(O)OR^6$, —$S(O)_mR^6$, —$S(O)_mNR^7R^8$ and —$NR^7R^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;
n is 0, 1, 2 or 3;
p is 0, 1, 2, 3, 4 or 5;
q is 0, 1 or 2; and
x is 0, 1, 2 or 3.

Preferably, the EZH2 inhibitor is a compound of formula (IA)

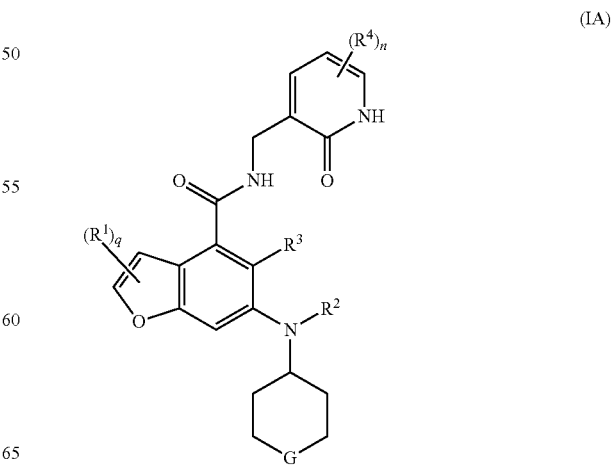

or a pharmaceutically acceptable salt thereof or a stereoisomer thereof, wherein, G is selected from the group consisting of $CR^bR^c$, C=O, $NR^d$, $S(O)_m$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —$C(O)R^6$, —$C(O)OR^6$, —$S(O)_mR^6$ and —$NR^7R^8$;

$R^d$ is selected from the group consisting of hydrogen, alkyl, cycloalkyl, haloalkyl, hydroxyalkyl, heterocyclyl, aryl, heteroaryl, —$C(O)R^6$, —$C(O)OR^6$ and —$S(O)_mR^6$; and $R^1$ to $R^4$, $R^6$ to $R^8$, n, m and q are as defined in formula (I).

Further preferably, the EZH2 inhibitor is a compound of formula (IB)

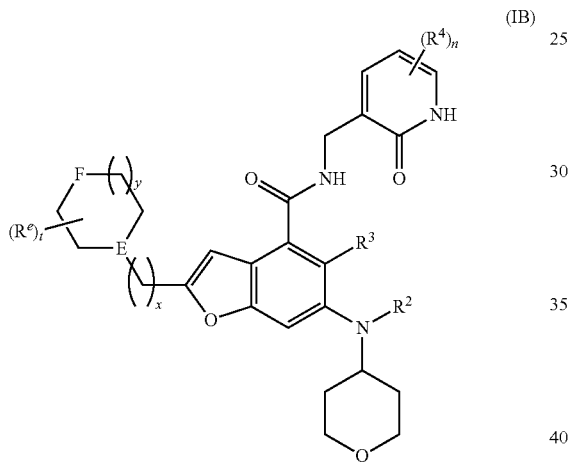

or a pharmaceutically acceptable salt thereof, wherein,

E is CH or nitrogen;

F is selected from the group consisting of $CR^bR^c$, C=O, $NR^d$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —$OR^6$, —$C(O)R^6$, —$C(O)OR^6$, —$S(O)_mR^6$ and —$NR^7R^8$;

$R^d$ is selected from the group consisting of hydrogen, alkyl, cycloalkyl, haloalkyl, hydroxyalkyl, heterocyclyl, aryl, heteroaryl, —$C(O)R^6$, —$C(O)OR^6$ and —$S(O)_mR^6$;

each $R^e$ is identical or different and each is independently selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

t is 0, 1, 2, 3, 4 or 5;

x is 0, 1, 2 or 3;

y is 0, 1, 2 or 3; and $R^2$ to $R^4$, $R^6$ to $R^8$, m and n are as defined in formula (I).

Further preferably, the EZH2 inhibitor is a compound of formula (IC)

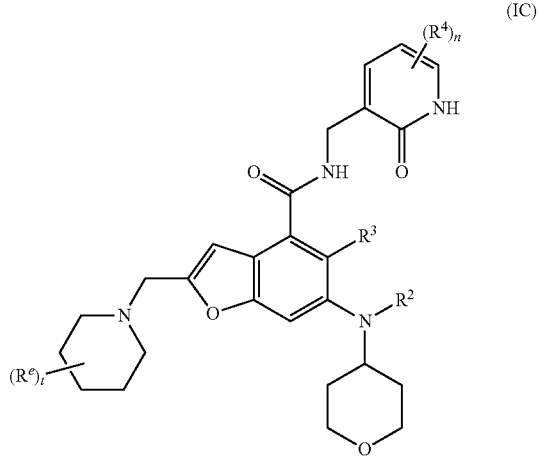

or a pharmaceutically acceptable salt thereof, wherein, each $R^e$ is identical or different and is independently selected from the group consisting of hydrogen, alkyl and halogen;

t is 0, 1, 2, 3, 4 or 5; and $R^2$ to $R^4$ and n are as defined in formula (I).

Further preferably, the EZH2 inhibitor is a compound of formula (ID)

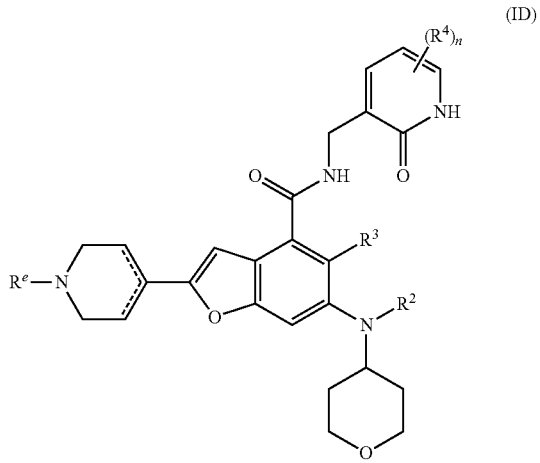

or a pharmaceutically acceptable salt thereof, wherein, $R^e$ is selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl; and $R^2$ to $R^4$ and n are as defined in formula (I), More preferably, the EZH2 inhibitor is a compound of formula (IE)

(IE)

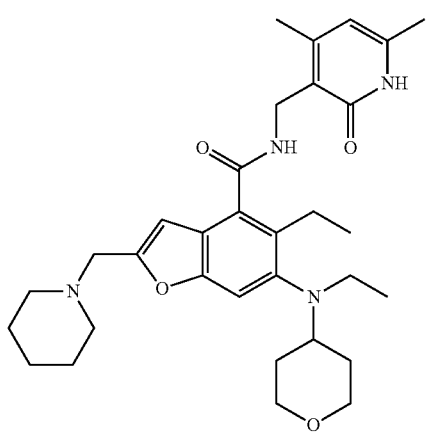

or a pharmaceutically acceptable salt thereof.

In the above embodiments, the BTK inhibitor is a compound of formula (II)

(II)

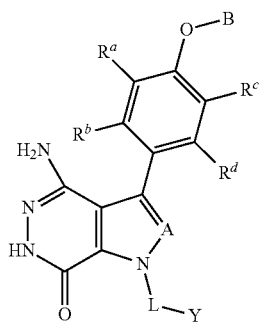

or a pharmaceutically acceptable salt thereof or a stereoisomer thereof,
wherein,
A is selected from the group consisting of $CR^1$ and N;
$R^1$ is selected from the group consisting of hydrogen, halogen and optionally substituted alkyl, wherein the substituent is selected from the group consisting of halogen, hydroxy, cyano, nitro, carboxy, amino, alkyl, alkoxy and haloalkyl;
$R^a$, $R^b$, $R^c$ and $R^d$ are each independently selected from the group consisting of hydrogen, halogen, hydroxy, cyano, nitro, optionally substituted alkyl and optionally substituted alkoxy, wherein the substituent is selected from the group consisting of halogen, hydroxy, cyano, nitro, carboxy, amino, alkyl, alkoxy and haloalkyl;
B is selected from the group consisting of hydrogen, optionally substituted cycloalkyl, optionally substituted heterocyclyl, optionally substituted aryl and optionally substituted heteroaryl, wherein the substituent is selected from the group consisting of halogen, hydroxy, cyano, nitro, carboxy, amino, alkyl, alkoxy and haloalkyl;
L is selected from the group consisting of a bond and optionally substituted alkyl; and
Y is selected from the group consisting of optionally substituted cycloalkyl, optionally substituted heterocyclyl, optionally substituted aryl and optionally substituted heteroaryl, wherein the substituent is selected from the group consisting of halogen, hydroxy, cyano, nitro, carboxy, amino, alkyl, alkylcarbonyl, alkynylcarbonyl and haloalkyl.

Preferably, the BTK inhibitor is a compound of formula (IIA)

(IIA)

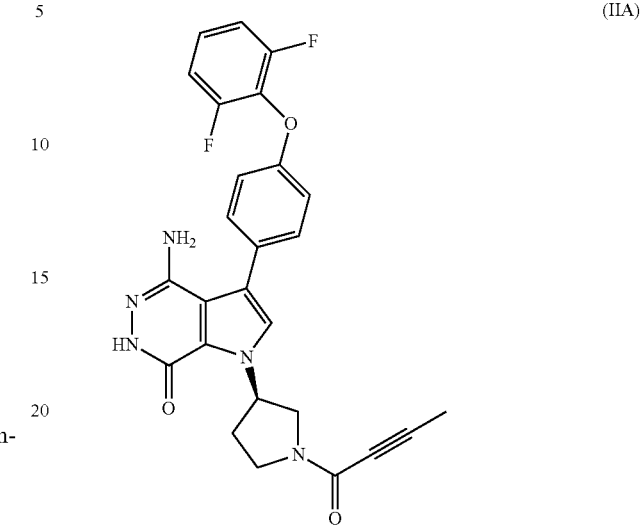

or a pharmaceutically acceptable salt thereof.

In an embodiment of the present invention, the pharmaceutically acceptable salt is selected from the group consisting of phosphate, hydrochloride, methanesulfonate, maleate, malate, p-toluenesulfonate and besylate.

In another embodiment of the present invention, the BTK inhibitor is selected from the group consisting of Ibrutinib, Acalabrutinib, MSC-2364447, Spebrutinib, HM-71224, Plevitrexed, GS-4059, GDC-0853, SNS-062, CGP-53716, Idoxifene, BTG-511, Banoxantrone, Glucarpidase, Antidigoxin polyclonal antibody, Crotalidae polyvalent immune Fab (ovine, BTG) and Otelixizumab.

In the above embodiments, the combination optionally comprises a third component selected from the group consisting of HDAC inhibitor, CDK4/6 inhibitor, ALK inhibitor, JAK2 inhibitor, Bcl-2 inhibitor, Hsp90 inhibitor, glucocorticoid, vinca alkaloid, antimetabolite, DNA damaging agent, Lenalidomide, Rituximab, PKC perturbagen, Lyn/Fyn inhibitor, Syk inhibitor, PI3K inhibitor, PKCβ inhibitor, IKK inhibitor, 20 s proteasome, IRF-4, IRAK4 antibody, CXCR4 antibody, CXCR5 antibody, GLS antibody, PLK antibody, CD20 antibody, Topo II inhibitor, DNA methyltransferase inhibitor, Ras/MAPK inhibitor and FGFR1 inhibitor; wherein the HDAC inhibitor is preferably selected from the group consisting of Panobinostat Lactate, Belinostat, Chidamide, Romidepsin, Vorinostat, Bexanostat and Entinostat; the CDK4/6 inhibitor is preferably selected from the group consisting of Palbociclib, Blinatumomab, Tiagabine Hydrochloride and Itolizumab; the Bcl-2 inhibitor is preferably selected from the group consisting of Venetoclax, Oblimersen sodium, ABT-737 and HA14-1; the Hsp90 inhibitor is preferably selected from the group consisting of Sebelipase alfa and Retaspimycin Hydrochloride; the JAK2 inhibitor is preferably selected from the group consisting of Tofacitinib citrate, Ruxolitinib Phosphate, Lestaurtinib, Momelotinib Dihydrochloride, Peficitinib and Filgotinib; the PKC perturbagen is preferably selected from the group consisting of Teprenone, Truheal, HO/03/03, Sotrastaurin, Enzastaurin and GF109203X; the ALK inhibitor is preferably selected from the group consisting of Alectinib hydrochloride, Ceritinib, Crizotinib, Bendamustine, Carmustine, Lumostine, chlormethine hydrochloride and NYP-TAE684; the PI3K inhibitor is preferably selected from the group consisting of GS-1101, IPI-145, BKM120, BEZ235, GDC-0941, AMG319, CAL-101 and A66; the IKK inhibitor is preferably selected from the group consisting of Auranofin, BAY 86-9766 and RDEA-119.

In the above embodiments, the combination has a synergistic effect.

The present invention provides a method for treating tumors, comprising administrating to a patient the above EZH2 inhibitor and BTK inhibitor.

According to the use of the present invention, the tumor is lymphoma, preferably non-Hodgkin lymphoma, and more preferably B cell proliferative disease; wherein the B cell proliferative disease is selected from the group consisting of diffuse large B-cell lymphoma (DLBCL), chronic lymphocytic leukemia (CLL), small lymphocytic lymphoma (SLL), high-risk CLL or non-CLL/SLL lymphoma, follicular lymphoma (FL), mantle cell lymphoma (MCL), precursor B cell tumor, precursor B lymphoblastic leukemia (or lymphoma), mature (peripheral) B cell tumor, lymphoplasmacytic lymphoma (or immunoblastom), extranodal mucosa-associated lymphoma, hairy cell leukemia, plasmacytoma (or plasma cell myeloma), Waldenstrom's macroglobulinemia, multiple myeloma, marginal zone lymphoma, Burkitt's lymphoma (BL), non-Burkitt high grade B cell lymphoma or extranodal marginal zone B-cell lymphoma, acute or chronic myelogenous (or myeloid) leukemia, myelodysplastic syndrome and acute lymphoblastic leukemia.

The present invention provides a combination of the above EZH2 inhibitor and the above BTK inhibitor for use as a medicament for treating tumors.

According to the use of the present invention, the ratio of the EZH2 inhibitor to the BTK inhibitor is 0.001-1000, preferably 0.01-100, further preferably 0.1-10, and more preferably 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 2:1, 2:3, 2:5, 2:7, 2:9, 2:11, 2:13, 2:15, 2:17, 2:19, 2:21, 3:1, 3:2, 3:4, 3:5, 3:7, 3:8, 3:10, 3:11, 3:13, 3:14, 3:16, 3:17, 3:19, 3:20, 4:1, 4:3, 4:5, 4:7, 4:9, 4:11, 4:13, 4:15, 4:17, 4:19, 4:21, 5:1, 5:2, 5:3, 5:4, 5:6, 5:7, 5:8, 5:9, 5:11, 5:12, 5:13, 5:14, 5:16, 5:17, 5:18, 5:19, 5:21, 6:1, 6:5, 6:7, 6:11, 6:13, 6:17, 6:19, 7:1, 7:2, 7:3, 7:5, 7:6, 7:8, 7:9, 7:10, 7:11, 7:12, 7:13, 7:15, 7:16, 7:17, 7:18, 7:19, 7:20, 8:1, 8:3, 8:5, 8:7, 8:9, 8:11, 8:13, 8:15, 8:17, 8:19, 9:1, 9:2, 9:4, 9:5, 9:7, 9:8, 9:10, 9:11, 9:13, 9:14, 9:16, 9:17, 9:19, 9:20, 10:1, 10:3, 10:7, 10:9, 10:11, 10:13, 10:17, or 10:19.

According to the use of the present invention, the EZH2 inhibitor is 0.1-5000 mg, and preferably 1-2000 mg.

According to the use of the present invention, the BTK inhibitor is 0.1-2000 mg, and preferably 1-1000 mg.

In the present invention, the administration dose of the EZH2 inhibitor is 0.1-5000 mg, and preferably 10 mg, 50 mg, 100 mg, 150 mg, 200 mg, 250 mg, 300 mg, 350 mg, 400 mg, 400 mg, 500 mg, 550 mg, 600 mg, 650 mg, 700 mg, 750 mg, 800 mg, 8500 mg, 900 mg, 950 mg, 1000 mg, 1200 mg, 1250 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3500 mg, 4000 mg, 4500 mg, or 5000 mg; the administration dose of the BTK inhibitor is 0.1-2000 mg, and preferably 10 mg, 20 mg, 30 mg, 50 mg, 80 mg, 90 mg, 100 mg, 150 mg, 160 mg, 200 mg, 250 mg, 300 mg, 350 mg, 500 mg, 650 mg, 700 mg, 750 mg, 800 mg, 850 mg, 900 mg, 950 mg, 1000 mg 1200 mg, 1300 mg, 1400 mg, 1500 mg, 1600 mg, 1800 mg, 1900 mg, or 2000 mg.

The administration mode of the combination of the present invention is selected from the group consisting of: simultaneous administration, co-administration after separate formulation, and sequential administration after separate formulation.

The present invention further relates to a use of a combination of an EZH2 inhibitor and a BTK inhibitor in the preparation of a medicament for treating tumors, wherein the recommended administration frequency of the EZH2 inhibitor is once a day or twice a day, and the recommended administration frequency of the BTK inhibitor is once a day.

Significantly, the combination of the EZH2 inhibitor and the BTK inhibitor of the present invention has a synergistic effect.

The present invention also relates to a pharmaceutical composition of an EZH2 inhibitor and a BTK inhibitor optionally comprising one or more pharmaceutically acceptable carriers, excipients and/or diluents. The pharmaceutical composition can be formulated into any one of the pharmaceutically acceptable dosage forms. For example, a pharmaceutical formulation of an EZH2 inhibitor and a BTK inhibitor can be formulated into a tablet, capsule, pill, granule, solution, suspension, syrup, injection (including injection solution, sterile powder for injection and concentrated solution for injection), suppository, inhalant or spray.

In addition, the pharmaceutical composition of the present invention can also be administrated to a patient or subject in need of such treatment by any suitable administration mode, for example, oral, parenteral, rectal, intrapulmonary or topical administration. For oral administration, the pharmaceutical composition can be formulated into an oral formulation, for example, an oral solid formulation such as a tablet, capsule, pill, granule and the like; or an oral liquid formulation such as an oral solution, oral suspension, syrup and the like. When formulated into an oral formulation, the pharmaceutical composition can further comprise a suitable filler, binder, disintegrant, lubricant and the like.

The pharmaceutical composition of the EZH2 inhibitor and the BTK inhibitor of the present invention can be administrated alone, or in combination with one or more therapeutic agents. Accordingly, in certain preferred embodiments, the pharmaceutical composition further comprises one or more therapeutic agents.

The components to be combined (for example, the EZH2 inhibitor, the BTK inhibitor and a second therapeutic agent) can be administrated simultaneously or sequentially separately. For example, the second therapeutic agent can be administrated before, at the same time of, or after the co-administration of the EZH2 inhibitor and the BTK inhibitor of the present invention. Moreover, the components to be combined can also be co-administrated in the same formulation or in separate and different formulations.

In the present invention, the term "combined administration" or "co-administration" is an administration mode, including various situations in which the two drugs are administrated sequentially or simultaneously. The term "simultaneously" herein means that the EZH2 inhibitor and the BTK inhibitor are administrated during the same administration cycle, for example, the two chugs are administrated within two days or one day. The term "sequential or successive" administration includes situations in which the EZH2 inhibitor and the BTK inhibitor are administrated respectively in different administration cycles. These administration modes all belong to the combined administration of the present invention.

The term "effective amount" of the present invention encompasses an amount sufficient to ameliorate or prevent a symptom or sign of a medical condition. The term "effective amount" also refers to an amount sufficient to allow or facilitate diagnosis. An effective amount for a particular patient or veterinary subject may vary depending on factors such as the condition to be treated, the general health of the patient, the route and dose of administration, and the severity of side effects. An effective amount can be a maximal dose or an administration regimen that avoids significant side effects or toxic effects.

Definitions

In the specification and claims of the present application, unless otherwise indicated, the scientific and technical terms used herein have the meanings generally understood by a person skilled in the art. However, in order to understand the present invention better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "halogen" or "halogen atom" used in the present invention refers to fluorine atom, chlorine atom, bromine atom or iodine atom.

The term "cyano" used in the present invention refers to a —CN group.

The term "hydroxy" used in the present invention refers to an —OH group.

The term "amino" used in the present invention refers to a —NH group.

The term "carboxy" used in the present invention refers to a —COOH group.

The term "carbonyl" used in the present invention refers to a —CO— group.

The term "nitro" used in the present invention refers to a —NO$_2$ group.

The term "alkyl" used in the present invention refers to a linear or branched alkyl having 1 to 20 carbon atoms, including for example "C$_{1-6}$ alkyl", "C$_{1-4}$ alkyl" and the like. The specific examples of alkyl include, but are not limited to: methyl, ethyl, n-propyl, isopropyl, n-butyl, isobutyl, sec-butyl, tert-butyl, n-pentyl, isopentyl, 2-methylbutyl, neo-pentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "alkynyl" used in the present invention refers to a linear or branched alkynyl having 2 to 20 carbon atoms and at least one carbon-carbon triple bond, including for example "C$_{2-6}$ alkynyl", "C$_{2-4}$ alkynyl" and the like. The examples of alkynyl include, but are not limited to: ethynyl, propynyl, 2-butynyl, 2-pentynyl, 3-pentynyl, 4-methyl-2-pentynyl, 2-hexynyl, 3-hexynyl, 5-methyl-2-hexynyl and the like.

The term "cycloalkyl" used in the present invention refers to a saturated or partially unsaturated monocyclic or polycyclic hydrocarbon group having 3 to 14 carbon atoms, preferably 3 to 12 carbon atoms, more preferably 3 to 8 carbon atoms, most preferably 5 to 6 carbon atoms, and the cycloalkyl is most preferably cyclopropyl. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, and preferably cyclopropyl, or cyclohexenyl. Polycyclic cycloalkyl includes a cycloalkyl having a spiro ring, fused ring or bridged ring.

The term "fused cycloalkyl" used in the present invention refers to a cyclic structure having 4 to 15 carbon atoms, which is formed with two or more cyclic structures attached to each other by two adjacent atoms. The fused cycloalkyl includes for example "6 to 11 membered fused cycloalkyl", "5 to 9 membered fused cycloalkyl", "7 to 10 membered fused cycloalkyl", "9 to 10 membered fused cycloalkyl" and the like. Optionally, the carbon atoms of the cyclic structure can be oxidized. The examples of fused cycloalkyl include, but are not limited to:

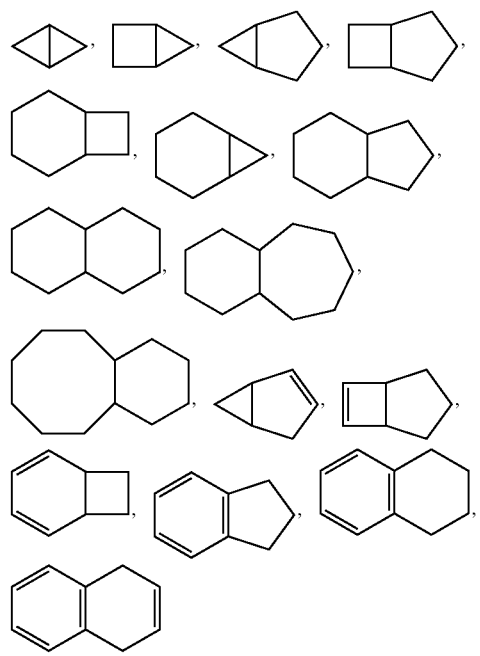

and the like.

The term "Spiro cycloalkyl" used in the present invention refers to a cyclic structure having 5 to 15 ring carbon atoms, which is formed with two or more cyclic structures attached to each other by one carbon atom. Optionally, the carbon atoms of the cyclic structure can be oxidized. The spiro cycloalkyl includes, for example, "6 to 11 membered spiro cycloalkyl", "5 to 10 membered spiro cycloalkyl", "7 to 8 membered spiro cylyl", "9 to 10 membered spiro cycloalkyl" and the like. The specific examples of spiro cycloalkyl include, but are not limited to:

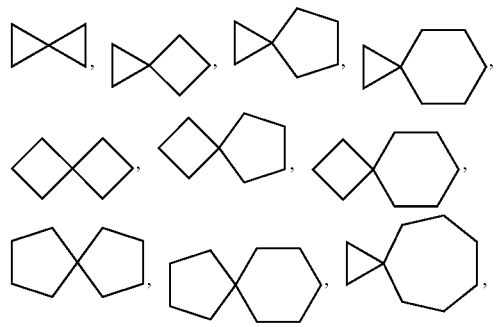

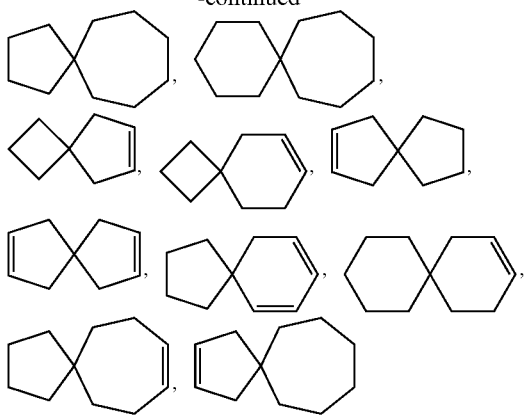

and the like.

The term "bridged cycloalkyl" used in the present invention refers to a cyclic structure having 5 to 15 ring carbon atoms, which is formed with two or more cyclic structures attached to each other by two non-adjacent carbon atoms. Optionally, the carbon atoms of the cyclic structure can be oxidized. The bridged cycloalkyl includes, for example, "6 to 11 membered bridged cycloalkyl", "7 to 10 membered bridged cycloalkyl", "9 to 10 membered bridged cycloalkyl" and the like. The specific examples of bridged cycloalkyl include, but are not limited to:

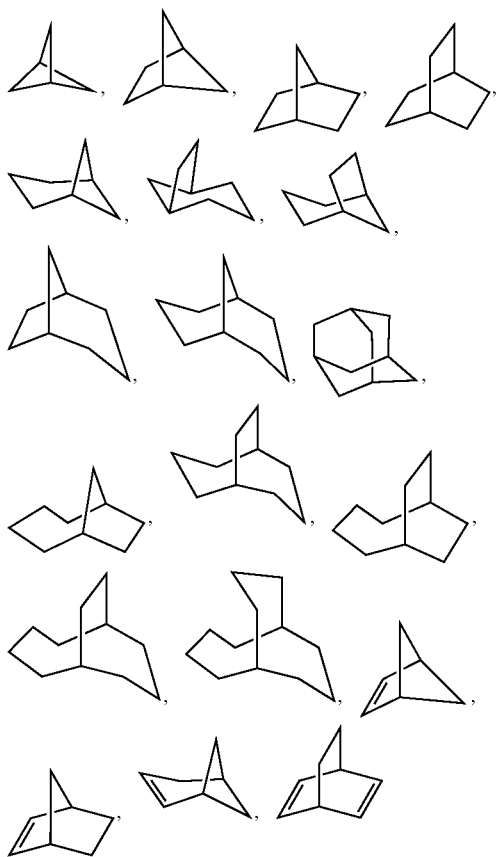

and the like.

The term "heterocyclyl" used in the present invention refers to a 3 to 14 membered saturated or partially unsaturated monocyclic or polycyclic hydrocarbon group, wherein one or more ring atoms are heteroatoms selected from the group consisting of N, O and S(O)$_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, more preferably 3 to 8 ring atoms, and more preferably 5 to 6 ring atoms. Non-limited examples of monocyclic heterocyclyl include pyrrolidinyl, piperidinyl, piperazinyl, morpholinyl, thiomorpholinyl, homopiperazinyl, pyranyl, tetrahydrofuranyl and the like. Polycyclic heterocyclyl includes a heterocyclyl having a spiro ring, fused ring or bridged ring.

The term "fused heterocyclyl" used in the present invention refers to a cyclic structure having 4 to 15 ring atoms (wherein at least one ring atom is heteroatom, for example, nitrogen atom, oxygen atom or sulfur atom), which is formed with two or more cyclic structures attached to each other by two adjacent atoms. Optionally, the ring atoms (for example, carbon atoms, nitrogen atoms or sulfur atoms) of the cyclic structure can be oxidized. The fused heterocyclyl includes, for example, "4 to 12 membered fused heterocyclyl", "5 to 9 membered fused heterocyclyl", "6 to 11 membered fused heterocyclyl", "7 to 9 membered fused heterocyclyl", "9 to 10 membered fused heterocyclyl" and the like. The specific examples of fused heterocyclyl include, but are not limited to: pyrrolidinocyclopropyl, cyclopentanoazacyclopropyl, pyrrolidinocyclobutyl, pyrrolidinopyrrolidinyl, pyrrolidinopipericlyl, pyrrolidinopiperazinyl, pyrrolidinomorpholinyl, piperdinomorpholinyl, benzopyrrolidinyl, tetrahydroimidazo[4,5-c]pyridyl, 3,4-dihydroquinazolinyl, 1,2-dihydroquinoxalinyl, benzo[d][1,3]dioxacyclopentenyl, 1,3-dihydroisobenzofuryl, 2H-chromenyl, 2-oxo-2H-chromenyl, 4H-chromenyl, 4-oxo-4H-chromenyl, chromanyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, benzoimidazolidinyl, octahydro-benzo[d]imidazolyl, decahydroquinolyl, hexahydrothienoimidazolyl, hexahydrofuroimidazolyl, 4,5,6,7-tetrahydro-1H-benzo[d]imidazolyl, octahydrocyclopenteno[c]pyrrolyl, dihyclroindolyl, dihydroisoindolyl, benzoxazolidinyl, benzothiazolidinyl, 1,2,3,4-tetrahydroisoquino 1,2,3,4-tetrahydroquinolyl, 4H-1,3-benzooxazinyl and the like.

The term "spiro heterocyclyl" used in the present invention refers to a cyclic structure having 5 to 15 ring atoms (wherein at least one ring atom is heteroatom, for example, nitrogen atom, oxygen atom or sulfur atom), which is formed with two or more cyclic structures attached to each other by one ring atom. Optionally, the ring atoms (for example, carbon atoms, nitrogen atoms or sulfur atoms) of the cyclic structure can be oxidized. The spiro heterocyclyl includes, for example, "5 to 11 membered spiro heterocyclyl", "6 to 11 membered spiro heterocyclyl", "6 to 9 membered spiro heterocyclyl", "9 to 10 membered spiro heterocyclyl" and the like. The specific examples of spiro heterocyclyl include, but are not limited to:

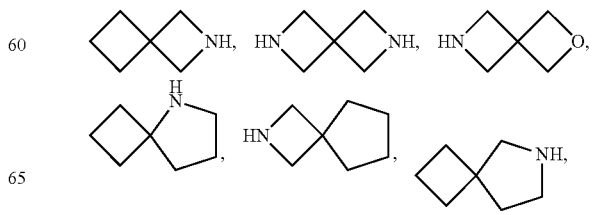

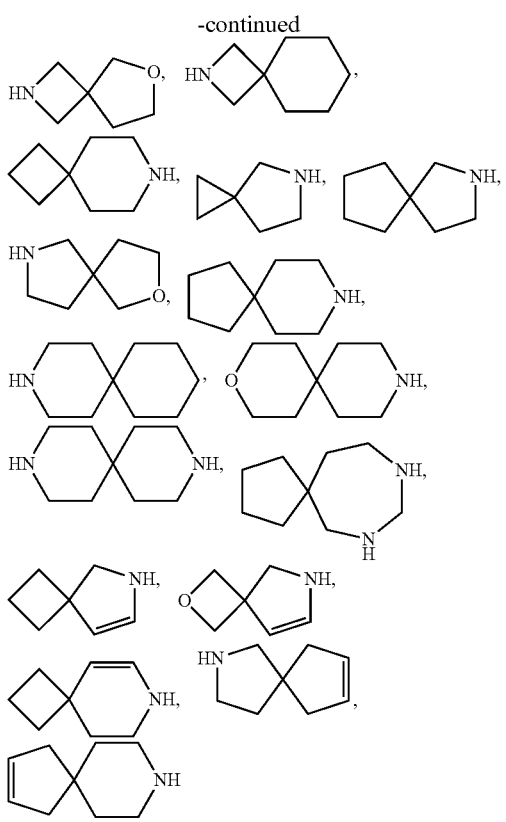

and the like.

The term "bridged heterocyclyl" used in the present invention refers to a cyclic structure having 5 to 15 ring atoms (wherein at least one ring atom is heteroatom, for example, nitrogen atom, oxygen atom or sulfur atom), which is formed with two or more cyclic structures attached to each other by two non-adjacent ring atoms. Optionally, the ring atoms (for example, carbon atoms, nitrogen atoms or sulfur atoms) of the cyclic structure can be oxidized. The bridged heterocyclyl includes, for example, "5 to 10 membered bridged heterocyclyl", "6 to 11 membered bridged heterocyclyl", "6 to 9 membered bridged heterocyclyl", "7 to 9 membered bridged heterocyclyl" and the like. The specific examples of bridged heterocyclyl include, but are not limited to:

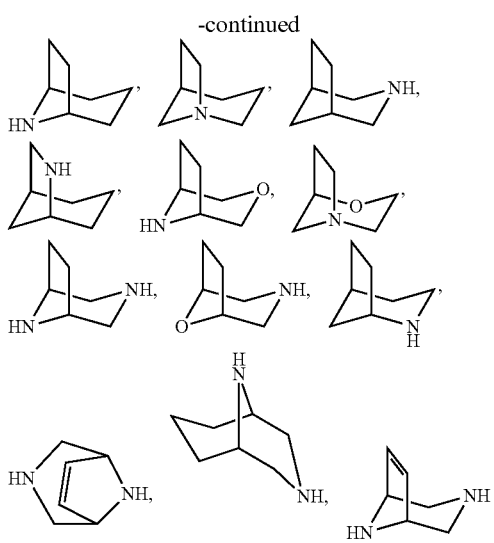

and the like.

The term "haloalkyl" used in the present invention refers to a group derived from "alkyl" in which one or more hydrogen atoms are substituted by one or more "halogen atoms", and the terms "halogen atom" and "alkyl" are as defined above.

The term "hydroxyalkyl" used in the present invention refers to a group derived from "alkyl" in which one or more hydrogen atoms are substituted by one or more "hydroxy", and the term "alkyl" is as defined above.

The terms "alkoxy, haloalkoxy, alkylcarbonyl, alkoxycarbonyl, alkylcarbonylamino, alkylaminocarbonyl, dialkylaminocarbonyl, alkylaminocarboxy, haloalkylcarbonyl, cycloalkylalkyl, cycloalkylcarbonyl, heterocyclylcarbonyl, alkylamino, alkylaminoalkyl or dialkylamino" used in the present invention refer to a group with a linkage form of alkyl-O—, haloalkyl-O—, alkyl-C(O)—, alkyl-O—C(O)—, alkyl-C(O)—NH—, alkyl-NH—C(O)—, (alkyl)$_2$-NH—C(O)—, alkyl-C(O)—O—, haloalkyl-C(O)—, cycloalkyl-alkyl-, cycloalkyl-C(O)—, heterocyclyl-C(O)—, alkyl-NH—, alkyl-NH-alkyl- or (alkyl)$_2$-N—, wherein the terms "alkyl, haloalkyl, cycloalkyl and heterocyclyl" are as defined above.

The term "aryl" used in the present invention refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 8 membered aryl, more preferably phenyl, anthryl and phenanthryl, and most preferably phenyl. The ring of aryl can be fused to the ring of heteroaryl, heterocyclyl or cycloalkyl, wherein the ring bound to the parent structure is the aryl ring. Non-limiting examples thereof include:

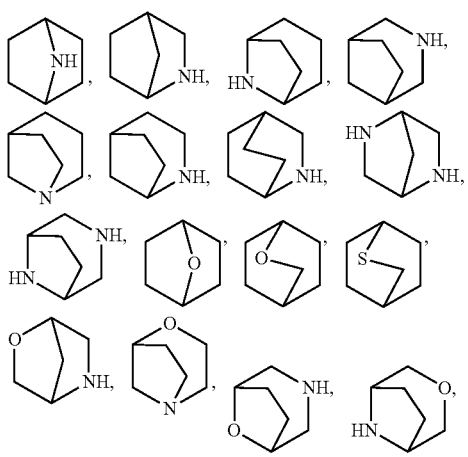

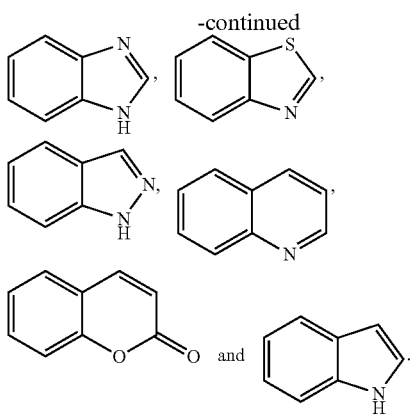

The term "heteroaryl" used in the present invention refers to a 5 to 15 membered all-carbon monocyclic ring or fused polycyclic ring group having a conjugated π-electron system, and further having 1 to 4 heteroatoms selected from the group consisting of O, S and N. The heteroaryl is preferably 5 to 8 membered heteroaryl, and more preferably 5 or 6 membered heteroaryl. The specific examples of heteroaryl include, but are not limited to, furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidyl, pyridazinyl, pyrazinyl, 1,2,3-triazinyl, 1,3,5-triazinyl, 1,2,4,5-tetrazinyl, azacycloheptatrienyl, 1,3-diazacycloheptatrienyl, azacyclooctatetraenyl and the like. The ring of heteroaryl can be fused to the ring of aryl, heterocyclyl or cycloalkyl, wherein the ring bound to the parent structure is the heteroaryl ring. Non-limiting examples thereof include:

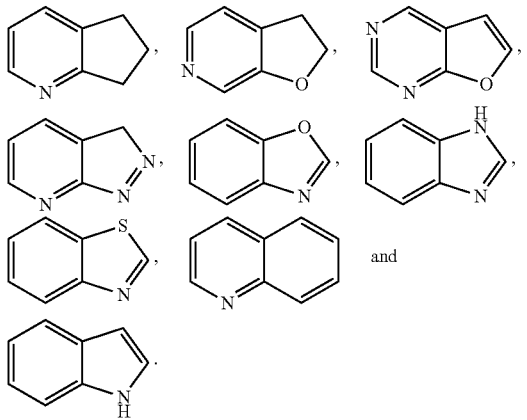

The expression "carbon atoms, nitrogen atoms or sulfur atoms are oxidized" used in the present invention refers to the formation of C=O, N=O, S=O or SO$_2$ structure.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

Advantageous Effects of the Present Invention

Compared with the prior art, the technical solution of the present invention has the following advantages:
The combined administration of the EZH2 inhibitor and the BTK inhibitor of the present invention has a significant inhibition effect on the proliferation of SU-DHL-4 and SU-DHL-6 cells, as well as a synergistic effect; the combined administration also has a significant inhibition effect on the proliferation of B cell lymphoma DOHH-2 cells, as well as a significant synergistic effect.

DETAILED DESCRIPTION OF THE INVENTION

Figure 1:
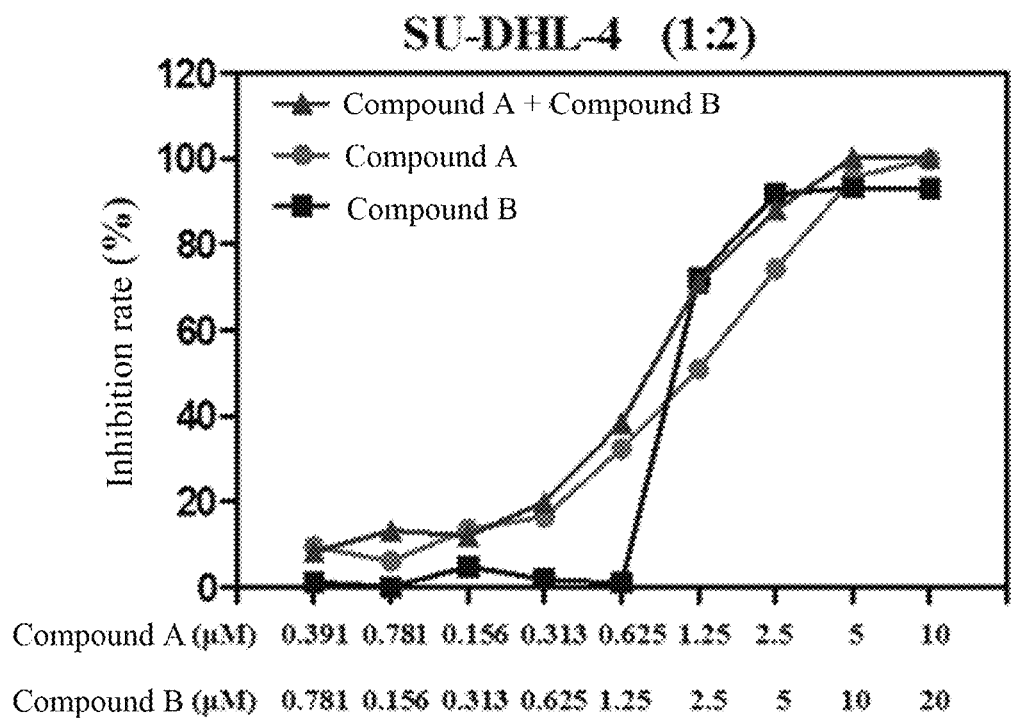
FIG. 1 shows the inhibition effect of the combined administration of an EZH2 inhibitor and a BTK inhibitor of the present invention (the molarity ratio of compound A to compound B=1:2) and the administration of single component (compound B, compound A) on the proliferation of SU-DHL-4 cells.
Figure 2:
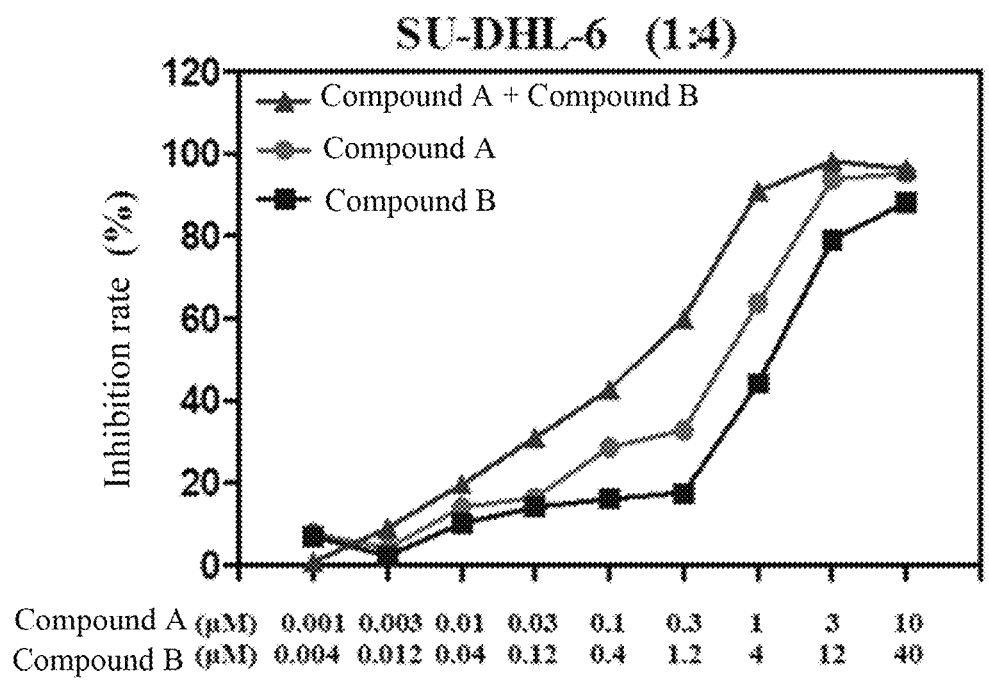
FIG. 2 shows the inhibition effect of the combined administration of an EZH2 inhibitor and a BTK inhibitor of the present invention (the molarity ratio of compound A to compound B=1:4) and the administration of single component (compound B, compound A) on the proliferation of SU-DHL-6 cells.

The exemplary experimental solutions for the medicinal use of the composition of the present invention in treating diabetes are provided below in order to demonstrate the favorable activity and beneficial technical effects of the composition of the present invention. However, it should be understood that the following experimental solutions are merely examples of the present invention and are not intended to limit the scope of the present invention. A person skilled in the art, based on the teachings of the specification, can make suitable modifications or alterations to the technical solutions of the present invention without departing from the spirit and scope of the present invention.

Comparative Example 1. Preparation of N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide represented by formula (IE) (compound B)
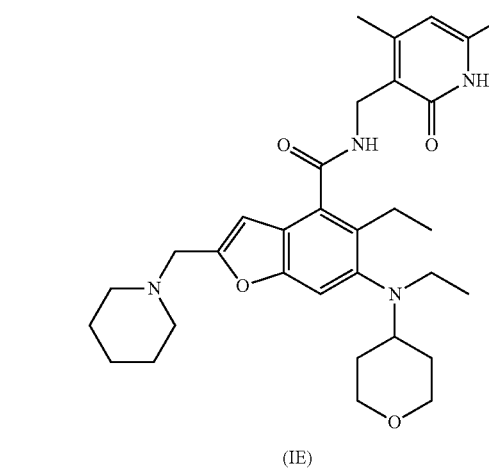
(IE)
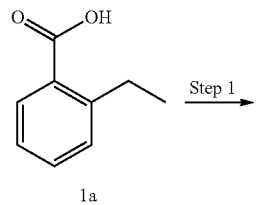
1a
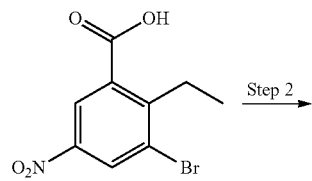
1b
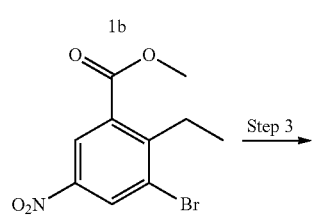
1c
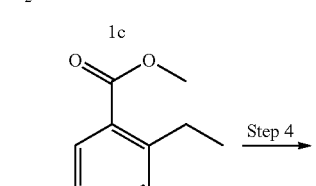
1d
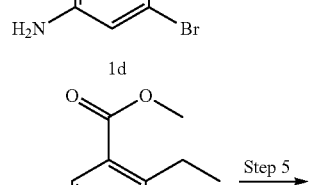
1e
-continued
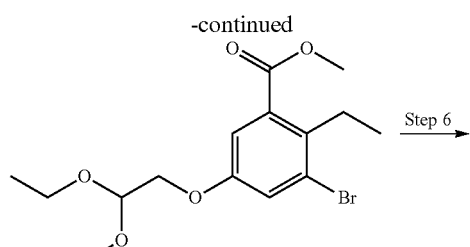
1f
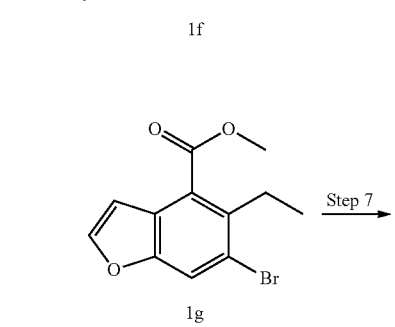
1g
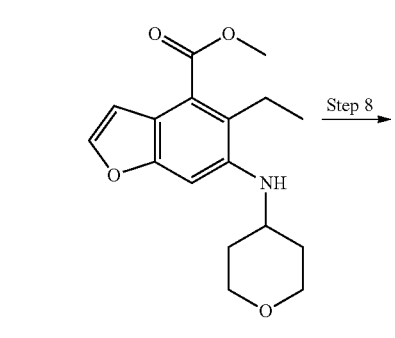
1h
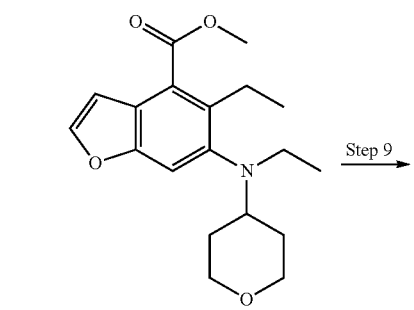
1i
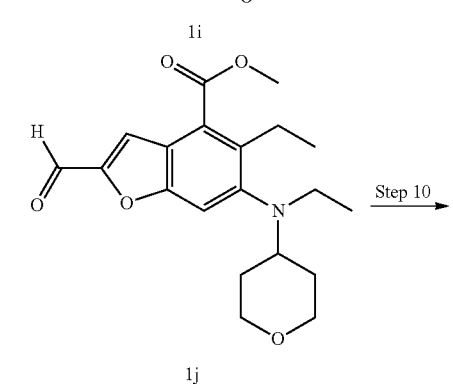
1j

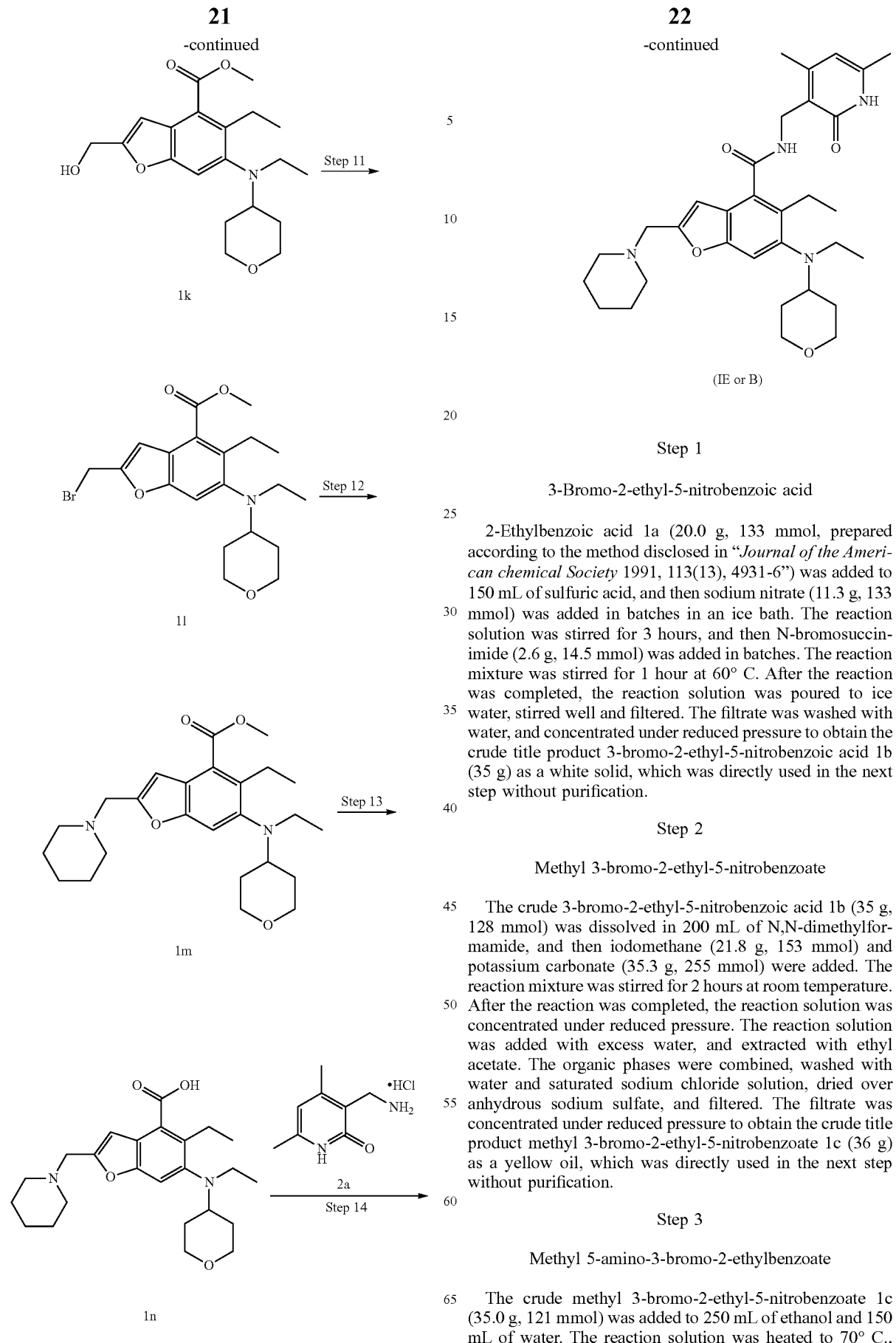

(IE or B)

Step 1

3-Bromo-2-ethyl-5-nitrobenzoic acid

2-Ethylbenzoic acid 1a (20.0 g, 133 mmol, prepared according to the method disclosed in "*Journal of the American chemical Society* 1991, 113(13), 4931-6") was added to 150 mL of sulfuric acid, and then sodium nitrate (11.3 g, 133 mmol) was added in batches in an ice bath. The reaction solution was stirred for 3 hours, and then N-bromosuccinimide (2.6 g, 14.5 mmol) was added in batches. The reaction mixture was stirred for 1 hour at 60° C. After the reaction was completed, the reaction solution was poured to ice water, stirred well and filtered. The filtrate was washed with water, and concentrated under reduced pressure to obtain the crude title product 3-bromo-2-ethyl-5-nitrobenzoic acid 1b (35 g) as a white solid, which was directly used in the next step without purification.

Step 2

Methyl 3-bromo-2-ethyl-5-nitrobenzoate

The crude 3-bromo-2-ethyl-5-nitrobenzoic acid 1b (35 g, 128 mmol) was dissolved in 200 mL of N,N-dimethylformamide, and then iodomethane (21.8 g, 153 mmol) and potassium carbonate (35.3 g, 255 mmol) were added. The reaction mixture was stirred for 2 hours at room temperature. After the reaction was completed, the reaction solution was concentrated under reduced pressure. The reaction solution was added with excess water, and extracted with ethyl acetate. The organic phases were combined, washed with water and saturated sodium chloride solution, dried over anhydrous sodium sulfate, and filtered. The filtrate was concentrated under reduced pressure to obtain the crude title product methyl 3-bromo-2-ethyl-5-nitrobenzoate 1c (36 g) as a yellow oil, which was directly used in the next step without purification.

Step 3

Methyl 5-amino-3-bromo-2-ethylbenzoate

The crude methyl 3-bromo-2-ethyl-5-nitrobenzoate 1c (35.0 g, 121 mmol) was added to 250 mL of ethanol and 150 mL of water. The reaction solution was heated to 70° C., added with ammonium chloride (52.8 g, 969 mmol), and then added with iron powder (34 g, 606 mmol) in batches. The reaction mixture was stirred for 2 hours at 70° C. After the reaction was completed, the reaction solution was filtered through celite while hot. The filter cake was washed with hot ethanol, and then the filtrate was combined and concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-amino-3-bromo-2-ethylbenzoate 1d (22.0 g, yield 70%) as a yellow solid.

Step 4

Methyl 3-bromo-2-ethyl-5-hydroxybenzoate

Methyl 5-amino-3-bromo-2-ethylbenzoate 1d (15.0 g, 58 mmol) was dissolved in 10 mL of acetonitrile, and then 200 mL of 10% sulfuric acid was added. The reaction solution was stirred well and cooled to 3° C. in an ice-salt bath, and then added dropwise with 10 mL of a pre-prepared solution of sodium nitrite (4.4 g, 64 mmol). The reaction solution was stirred for 4 hours at the above temperature, added dropwise with 200 mL of 50% sulfuric acid, and then stirred for 1 hour at 90° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 3-bromo-2-ethyl-5-hydroxybenzoate 1e (5.5 g, yield 37%) as a brown solid.

Step 5

Methyl 3-bromo-5-(2,2-diethoxyethoxy)-2-ethylbenzoate

Methyl 3-bromo-2-ethyl-5-hydroxybenzoate 1e (35 g, 135 mmol) was dissolved in 200 mL of N,N-dimethylformamide, and then 2-bromo-1,1-diethoxyethane (40 g, 202 mmol) and potassium carbonate (37 g, 269 mmol) were added. The reaction mixture was stirred at 120° C. for 12 hours. After the reaction was completed, the reaction solution was concentrated under reduced pressure to remove N,N-dimethylformamide. The reaction solution was added with water, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 3-bromo-5-(2,2-diethoxyethoxy)-2-ethylbenzoate 1f (40 g, yield 80%) as a light yellow oil.

Step 6

Methyl 6-bromo-5-ethylbenzofuran-4-carboxylate

Polyphosphoric acid (30 g) was added to 400 mL of toluene. The reaction solution was heated to 100° C., and added with 50 mL of a pre-prepared solution of methyl 3-bromo-5-(2,2-diethoxyethoxy)-2-ethylbenzoate 1f (40 g, 107 mmol) in toluene under stirring. The reaction solution was stirred for 16 hours at 100° C. After the reaction was completed, the supernatant was decanted. The residue was added with water and ethyl acetate. Two phases were separated, and the aqueous phase was extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 6-bromo-5-ethylbenzofuran-4-carboxylate 1g (11.8 g, yield 39%) as a yellow solid.

Step 7

Methyl 5-ethyl-6-((tetrahydro-2H-pyran-4-yl)amino) benzofuran-4-carboxylate

Methyl 6-bromo-5-ethylbenzofuran-4-carboxylate 1g (11.0 g, 39 mmol), tetrahydro-2H-pyran-4-amine (5.89 g, 58 mmol), tris(dibenzylideneacetone)dipalladium (3.6 g, 3.9 mmol), (0.9 mmol) bis(diphenylphosphino)-1,1'-binaphthalene (4.86 g, 7.8 mmol) and cesium carbonate (38 g, 117 mmol) were dissolved in 100 mL of toluene. The reaction solution was stirred for 12 hours at 100° C. After the reaction was completed, the reaction solution was filtered through celite, and the filter cake was washed with ethyl acetate. The organic phases were combined, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-((tetrahydro-2H-pyran-4-yl)amino)benzofuran-4-carboxylate 1h (10.0 g, yield 85%) as a yellow solid.

Step 8

Methyl 5-ethyl-6-(ethyl(tetrahydro-2H-pyran-4-yl) amino)benzofuran-4-carboxylate Methyl 5-ethyl-6-((tetrahydro-2H-pyran-4-yl)amino)benzofuran-4-carboxylate 1h (10.0 g, 0.033 mmol) was dissolved in 150 mL of 1,2-dichloroethane, and then acetaldehyde (7.2 g, 0.165 mmol) and acetic acid (9.9 g, 0.165 mmol) were added. The reaction solution was stirred for 1 hour, and added with sodium triacetoxyborohydride (20.8 g, 0.1 mmol). The reaction solution was stirred for 12 hours at room temperature. After the reaction was completed, the reaction solution was concentrated under reduced pressure, neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl(tetrahydro-2H-pyran-4-yl) amino)benzofuran-4-carboxylate 1i (7.8 g, yield 71%) as a white solid.

MS m/z (LC-MS): 332.4 [M+1]

Step 9

Methyl 5-ethyl-6-(ethyl(tetrahydro-2H-pyran-4-yl) amino)-2-formylbenzofuran-4-carboxylate Methyl 5-ethyl-6-(ethyl(tetrahydro-2H-pyran-4-yl) amino)benzofuran-4-carboxylate 1i (1.6 g, 4.8 mmol) was dissolved in 25 mL of tetrahydrofuran. The reaction solution was cooled to −70° C., and added dropwise with 2.0 M diisopropylamide (3.6 mL, 7.3 mmol) under an argon atmosphere. The reaction solution was stirred for 90 minutes, and added with N,N-dimethylformamide (536 mg, 7.3 mmol). The reaction solution was stirred for 2 hours, and then slowly warmed up to room temperature. The reaction solution was added with excess ammonium chloride, stirred well and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl (tetrahydro-2H-pyran-4-yl)amino)-2-formylbenzofuran-4-carboxylate 1j (1.3 g, yield 75%) as a yellow oil.

MS m/z (ESI):360.2 [M+1]

Step 10

Methyl 5-ethyl-6-(ethyl(tetrahydro-2H-pyran-4-yl) amino)-2-(hydroxymethyl)benzofuran-4-carboxylate Methyl 5-ethyl-6-(ethyl(tetrahydro-2H-pyran-4-yl) amino)-2-formylbenzofuran-4-carboxylate 1j (1.4 g, 3.9 mmol) was dissolved in 5 mL of tetrahydrofuran and 10 mL 4-carboxylate 1j (1.4 g, 3.9 mmol) was dissolved in 5 mL of tetrahydrofuran and 10 mL of methanol, and then sodium borohydride (222 mg, 5.8 mmol) was added. The reaction solution was stirred for 30 minutes at room temperature. After the reaction was completed, the reaction solution was concentrated under reduced pressure, added with water and saturated sodium bicarbonate solution, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl(tetrahydro-2H-pyran-4-yl) amino)-2-(hydroxymethyl)benzofuran-4-carboxylate 1k (1.4 g, yield 99%) as a yellow oil.

Step 11

Methyl 2-(bromomethyl)-5-ethyl-6-(ethyl(tetrahydro-2H-pyran-4-yl)amino)benzofuran-4-carboxylate Methyl 5-ethyl-6-(ethyl(tetrahydro-2H-pyran-4-yl) amino)-2-(hydroxymethyl)benzofuran-4-carboxylate 1k (1.0 g, 2.8 mmol) was dissolved in 30 mL of tetrahydrofuran, and then phosphorus tribromide (1.12 g, 4.2 mmol) was added dropwise. The reaction solution was stirred for 12 hours at room temperature. After the reaction was completed, the reaction solution was neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure to obtain the crude title product methyl 2-(bromomethyl)-5-ethyl-6-(ethyl(tetrahydro-2H-pyran-4-yl)amino)benzofuran-4-carboxylate 1l (1.15 g) as a yellow oil, which was directly used in the next step without purification.

Step 12

Methyl 5-ethyl-6-(ethyl(tetrahydro-2H-pyran-4-yl) amino)-2-(piperidin-1-ylmethyl)benzofuran-4-carboxylate The crude methyl 2-(bromomethyl)-5-ethyl-6-(ethyl(tetrahydro-2H-pyran-4-yl)amino)benzofuran-4-carboxylate 1l (1.15 g, 2.7 mmol) was dissolved in 15 mL of acetonitrile, and then 10 mL of a pre-prepared solution of piperidine (362 mg, 4.3 mmol) in acetonitrile were added dropwise. The reaction solution was stirred for 30 minutes at room temperature. After the reaction was completed, the reaction solution was concentrated under reduced pressure, and added with ethyl acetate and saturated sodium bicarbonate solution. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with dichloromethane and methanol as the eluent to obtain the title product methyl 5-ethyl-6-(ethyl(tetrahydro-2H-pyran-4-yl)amino)-2-(piperidin-1-ylmethyl)benzofuran-4-carboxylate 1m (1.2 g, yield 99%) as a yellow oil.

MS m/z (LC-MS): 429.2[M+1]

Step 13

5-Ethyl-6-(ethyl(tetrahydro-2H-pyran-4-yl)amino)-2-(piperidin-1-ylmethyl)benzofuran-4-carboxylic acid Methyl 5-ethyl-6-(ethyl(tetrahydro-2H-pyran-4-yl) amino)-2-(piperidin-1-ylmethyl)benzofuran-4-carboxylate 1m (1.2 g, 2.7 mmol) was dissolved in 5 mL of tetrahydrofuran and 20 mL of methanol, and then 5 mL of 4 M sodium hydroxide solution were added. The reaction solution was stirred for 12 hours at 60° C. After the reaction was completed, concentrated hydrochloric acid was added to adjust the pH of the reaction solution to 4. The mixture was concentrated under reduced pressure, and the residue was dissolved in a mixed solvent of dichloromethane and methanol (V:V=5:1) and filtered. The filter cake was washed with a mixed solvent of dichloromethane and methanol (V:V=5:1). The filtrates were combined and concentrated under reduced pressure to obtain the crude title product 5-ethyl-6-(ethyl(tetrahydro-2H-pyran-4-yl)amino)-2-(piperidin-1-ylmethyl)benzofuran-4-carboxylic acid 1n (1.1 g) as a yellow solid, which was directly used in the next step without purification.

MS m/z (LC-MS): 415.2[M+1]

Step 14

Preparation of the Compound of Formula (IE) (Defined as Compound B)

5-Ethyl-6-(ethyl(tetrahydro-2H-pyran-4-yl)amino)-2-(piperidin-1-ylmethyl)benzofuran-4-carboxylic acid 1n (1.0 g, 2.4 mmol) was dissolved in 30 mL of N,N-dimethylformamide, and then 1-ethyl-3-(3-dimethylaminopropyl)carbodiimide (696 mg, 3.6 mmol), 1-hydroxybenzotriazole (490 mg, 3.6 mmol) and N,N-diisopropylethylamine (1.56 g, 12.1 mmol) were added. The reaction solution was stirred for 1 hour, and then added with 3-(aminomethyl)-4,6-dimethylpyridin-2(1H)-one hydrochloride 2a (593 mg, 3.0 mmol, prepared according to the method disclosed in the patent application "WO2014097041"). The reaction solution was stirred for 12 hours at room temperature. After the reaction was completed, the reaction solution was added with excess water, and extracted with a mixed solvent of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by silica gel column chromatography with dichloromethane and methanol as the eluent to obtain the title product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide IE (750 mg, yield 57%) as a white solid.

MS m/z (ESI): 549.7 [M+1]

$^1$H-NMR (400 MHz, DMSO-$d_6$): δ 11.48 (s, 1H), 8.15 (t, 1H), 7.39 (s, 1H), 6.46 (s, 1H), 5.86 (s, 1H), 4.32 (d, 2H), 3.83 (d, 2H), 3.54 (s, 2H), 3.21 (t, 2H), 3.01-3.07 (m, 2H), 2.92-2.97 (m, 1H), 2.77-2.82 (m, 2H), 2.39 (brs, 4H), 2.23 (s, 3H), 2.11 (s, 3H), 1.64-1.67 (brd, 2H), 1.47-1.55 (m, 6H), 1.36-1.37 (brd, 2H), 1.02 (t, 3H), 0.82 (t, 3H).

Example 1. Effect of the Composition of the Present Invention on the Proliferation of DOHH-2 Cells In Vitro Test compounds: the compound of formula (IE) (defined as compound B, prepared according to the method disclosed in WO2017084494 (patent application PCT/CN2016/104318), see comparative example 1), and the compound of formula (IIA) (defined as compound A, prepared according to the method disclosed in the patent application WO2016007185A1).

Cell line: human B cell lymphoma DOHH-2 cells (purchased from DSMZ), cultured in vitro in RPMI 1640 medium containing 10% fetal bovine serum (FBS).

Formulation of Test Compound Solution:

Each of the test compounds was all formulated with DMSO into a 10 mM stock solution, which was formulated into the desired concentration with serum-free medium when used.

Experimental Method

A certain number of cells in logarithmic growth phase was inoculated in a 96-well culture plate. After 24 hours, the cells were added with the test compounds in different concentrations (1-100000 nM), and incubated for 72 hours. Each well was added with the MTT working solution. After 4 hours, the cells were lysed with the triple solution, and the OD value was measured at a wavelength of 570 nm by a microplate reader.

Data Analysis:

The cell growth inhibition rate was calculated by the following formula:

Inhibition rate=(OD value of control well−OD value of drug-administered well)/OD value of control well×100%;

The half effective concentration $IC_{50}$ was calculated using the non-linear regression method according to the inhibition rate of each concentration.

In the combined administration, the concentration ratio of compound A to compound B was 1:10. The combination index (CI) was calculated with Calcu-Syn program using the median effect method to evaluate the relationship between the two compounds during the combined administration (CI<1 refers to synergistic effect, CI=1 refers to additive effect, CI>1 refers to antagonistic effect).

Experimental Results

TABLE 1

Effect of single compound on the proliferation of DOHH-2 cells

| Compound | $IC_{50}$ (nM) |
|---|---|
| Compound A | 324.6 |
| Compound B | 5919.0 |

TABLE 2

Inhibition effect of the combined administration on the proliferation of DOHH-2 cells

| | CI | | |
|---|---|---|---|
| Compound | $ED_{50}$ | $ED_{75}$ | $ED_{90}$ |
| Compound A + Compound B | 0.09 | 0.09 | 0.09 |

Experimental Conclusion

It can be seen from the above table data that the combined administration of compound A and compound B has a synergistic inhibition effect on the proliferation of DOHH-2 cells in vitro.

Example 2. Effect of the Composition of the Present Invention on the Proliferation of SU-DHL-4 and SU-DHL-6 Cells In Vitro Test compounds: the compound of formula (IE) (defined as compound B, prepared according to the method disclosed in WO2017084494 (patent application PCT/CN2016/104318), see comparative example 1), and the compound of formula (IIA) (defined as compound A, prepared according to the method disclosed in the patent application WO2016007185A1).

Cell line: human B cell lymphoma SU-DHL-4 and SU-DHL-6 cells (purchased from ATCC), cultured in vitro in RPMI 1640 medium containing 10% fetal bovine serum (FBS).

Formulation of Test Compound Solution:

Each of the test compounds was all formulated with DMSO into a 10 mM stock solution, which was formulated into the desired concentration with serum-free medium when used.

Experimental Method

A certain number of cells in logarithmic growth phase was inoculated in a 96-well culture plate. After 24 hours, the cells were added with the test compounds in different concentrations (1-40000 nM), and incubated for 72 hours. Each well was added with the MTT working solution. After 4 hours, the cells were lysed with the triple solution (10% SDS, 5% isobutanol, 0.012 mol/L HCl) at 37° C. overnight, and the OD value was measured at a wavelength of 570 nm by a microplate reader.

Data Analysis:

The cell growth inhibition rate was calculated by the following formula:

Inhibition rate=(OD value of control well−OD value of drug-administered well)/OD value of control well×100%

The half effective concentration $IC_{50}$ was calculated using the non-linear regression method according to the inhibition rate of each concentration.

In the combined administration, the concentration ratio of compound A to compound B was 1:2 (for SU-DHL-4) and 1:4 (for SU-DHL-6). The combination index (CI) was calculated with Calcu-Syn program using the median effect method to evaluate the relationship between the two compounds during the combined administration (CI<1 refers to synergistic effect, CI=1 refers to additive effect, CI>1 refers to antagonistic effect).

Experimental Results

TABLE 3

Effect of single compound on the proliferation of SU-DHL-4 and SU-DHL-6 cells

| Cell line | $IC_{50}$(nM) | |
|---|---|---|
| | Compound A | Compound B |
| SU-DHL-4 | 1059 | 2169 |
| SU-DHL-6 | 711 | 4660 |

TABLE 4

Inhibition effect of the combined administration on the proliferation of SU-DHL-4 and SU-DHL-6 cells

| | CI | | |
|---|---|---|---|
| Compound A + Compound B | ED50 | ED75 | ED90 |
| SU-DHL-4 | 0.77 | 0.60 | 0.47 |
| SU-DHL-6 | 0.57 | 0.36 | 0.23 |

Experimental Conclusion

It can be seen from the above table date that the combined administration of compound A and compound B has a synergistic inhibition effect on the proliferation of SU-DHL-4 and SU-DHL-6 cells in vitro.

Example 3: Efficacy of the Composition of the Present Invention on the Subcutaneous Transplantation Tumor in Nude Mice Inoculated with the Human Follicular Lymphoma DOHH-2 Cells Test compounds: the compound of formula (IE) (defined as compound B, prepared according to the method disclosed in WO2017084494 (patent application PCT/CN2016/104318), see comparative example 1), and the compound of formula (IIA) (defined as compound A, prepared according to the method disclosed in the patent application WO2016007185A1).

Test animals: BALB/cA-nude nude mice, 5-6 weeks old, female, purchased from Shanghai Lingchang Biotechnology Co., Ltd., with laboratory animals use license No.: SCXK (Shanghai) 2013-0018 and animal certificate No.: 2013001818958, feeding condition: SPF grade.

Formulation of the Solution of the Test Compound:

The test compounds were all formulated with 0.2% Tween 80+0.5% CMC solutions, and diluted to the corresponding concentration.

Experimental Method (1) The nude mice were subcutaneously inoculated with lymphoma DOHH-2 cells. When the tumors grown to 100-200 mm$^3$, the animals were grouped randomly (D0). The dose and regimen of the administration are shown in Table 5.

(2) Observation and recording: the tumor volume was measured 2 to 3 times per week, the mice were weighed, and the data were recorded.

(3) Tumor measurement and endpoint

The endpoint is mainly dependent on whether the tumor growth is delayed or whether the mouse is cured. The tumor volume (in mm$^3$) was measured twice a week with caliper in two dimensions.

The tumor volume (V) is calculated as:

$$V=0.5 \times a \times b^2,$$

wherein a and b represent length and width, respectively;

$$T/C\ (\%)=(T-T_0)/(C-C_0) \times 100,$$

wherein T and C represent the tumor volume at the end of the experiment; $T_0$ and $C_0$ represent the tumor volume at the beginning of the experiment. The T/C value (percentage) is indicative of anti-tumor efficacy.

(4) Data analysis: the statistics were summarized, including mean and standard error of mean (SEM), statistical analysis of differences in tumor volume between groups, and analysis of data obtained by drug interaction that was carried out at the optimal treatment time point after the last administration (Day 21 after grouping). One-way variance analysis was performed to compare tumor volume and tumor weight between groups. When a non-significant F-statistic was obtained (p<0.001, treatment variance vs. error variance), the comparison between groups was performed using Games-Howell test. All data were analyzed using SPSS17.0, and P<0.05 was considered as statistically significant.

Experimental Results

TABLE 5

Effect of the combined administration on the proliferation of DOHH-2 cells

| Groups | Administration | Route | Mean tumor volume (mm³) D 0 | SEM | Mean tumor volume (mm³) D 21 | SEM | % T/C D 21 | % tumor inhibition rate D 21 | | P value D 21 | Number of animals in each group at the end of the experiment |
|---|---|---|---|---|---|---|---|---|---|---|---|
| Solvent | D 0-20 | PO, BID | 106.4 | ±1.6 | 1347.2 | ±178.2 | — | — | | — | 10 |
| Compound A 50 mg/kg | D 0-20 | PO, BID | 111.1 | ±2.3 | 742.0 | ±108.7 | 51 | 49 | * | 0.027 | 6 |
| Compound B 50 mg/kg | D 0-20 | PO, BID | 107.7 | ±4.4 | 914.1 | ±153.2 | 65 | 35 | * | 0.117 | 6 |
| Compound A 50 mg/kg + compound B 50 mg/kg | D 0-20 | PO, BID | 105.8 | ±3.4 | 414.2 | ±86.4 | 25 | 75 | | 0.002 | 6 |

D 0: the time of the first administration;
PO: oral administration;
BID: twice a day;
P value refers to comparison with solvent;
* P < 0.05, comparison with Compound A 50 mg/kg + compound B 50 mg/kg, with Student's t test; thee number of mice at the beginning of the test, solvent group n = 10, treatment group n = 6.

Experimental Conclusion

Figure 3:
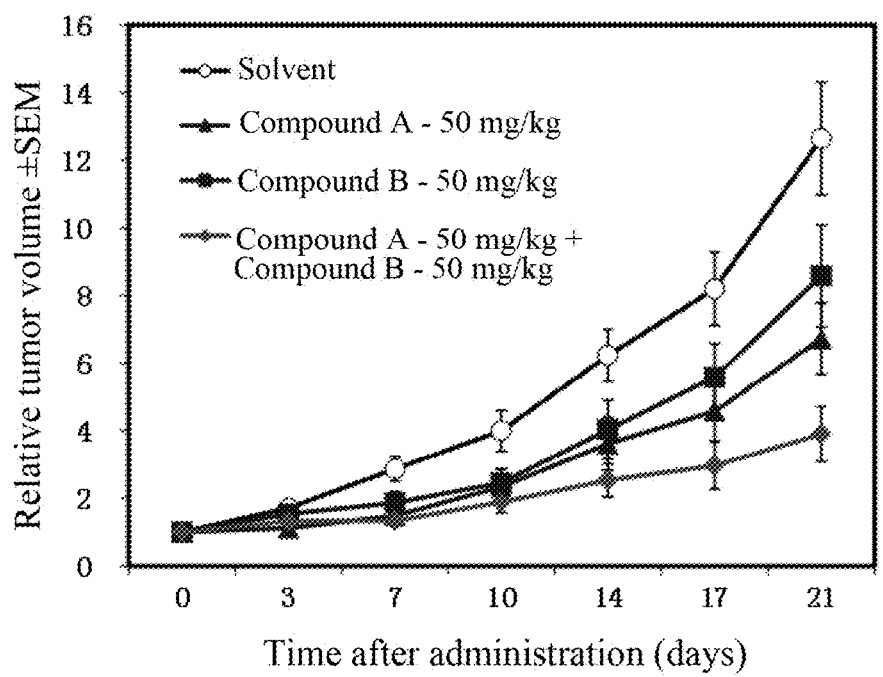
FIG. 3 shows the efficacy of the combined administration of an EZH2 inhibitor and a BTK inhibitor of the present invention (the combination of compound B and compound A) and the administration of single component (compound B, compound A) on the subcutaneous transplantation tumor in nude mice inoculated with lymphoma DOHH-2 cells.
Figure 4:
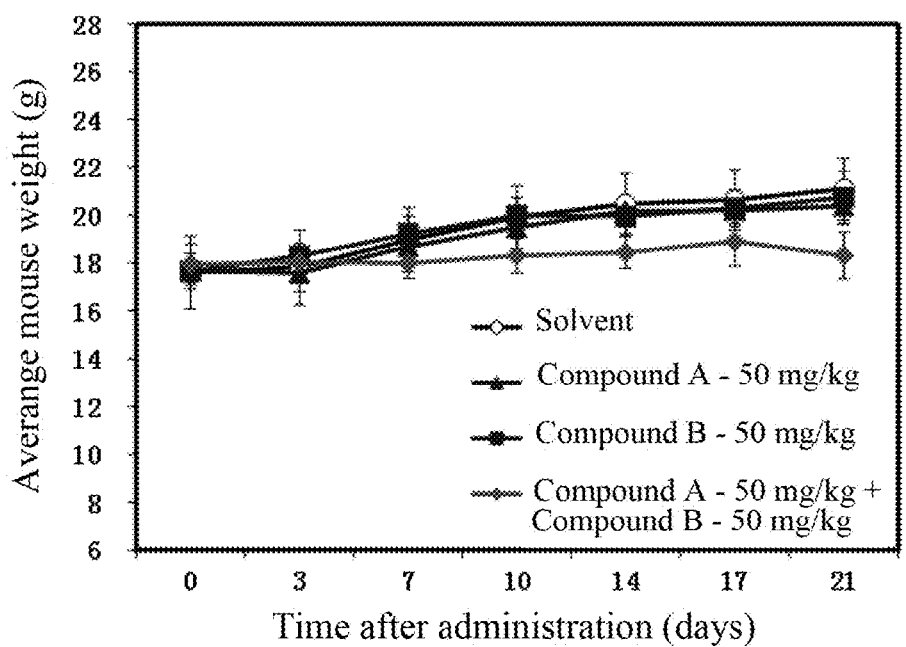
FIG. 4 shows the effect of the combined administration of an EZH2 inhibitor and a BTK inhibitor of the present invention (the combination of compound B and compound A) and the administration of single component (compound B, compound A) on the weight of nude mice subcutaneously inoculated with lymphoma DOHH-2 cells.

It can be seen from the data in Table 5 that compound A (50 mg/kg, PO, QD×21) inhibited the growth of the subcutaneous transplantation tumor in nude mice inoculated with DOHH-2 cells, and the tumor growth inhibition rate was 49% (P<0.05, compared with the solvent). Compound B (50 mg/kg, PO, QD×21) had a certain inhibition effect on DOHH-2 cells, and the tumor growth inhibition rate was 35% (P>0.05, compared with solvent). When the two compounds were administered in combination, the tumor growth inhibition rate was increased to 75% and the efficacy was significantly stronger than that of compound A or compound B alone (P<0.05, compared with single compound, see FIG. 3). FIG. 4 shows that the combination of compound A and compound B does not cause significant weight loss or other symptoms.

In summary, the combined effect of the BTK inhibitor compound A and the EZH2 inhibitor compound B of the present invention is better than the effect of single compound, and such a combination has a synergistic effect.

Example 4: Efficacy of the Composition of the Present Invention on the Subcutaneous Transplantation Tumor in Mice Inoculated with the Human B Cell Lymphoma SU-DHL-4 Cells Test compounds: the compound of formula (IE) (defined as compound B, prepared according to the method disclosed in WO2017084494 (patent application PCT/CN2016/104318), see comparative example 1), and the compound of formula (IIA) (defined as compound A, prepared according to the method disclosed in the patent application WO2016007185A1).

Test animals: SCID.BG mice, 5-6 weeks old, female, purchased from Shanghai Lingchang Biotechnology Co., Ltd., with laboratory animals use license No.: SCXK (Shanghai) 2013-0018 and animal certificate No.: 2013001820833, feeding condition: SPF grade.

Formulation of the Solution of the Test Compound:

The test compounds were all formulated with 0.2% Tween 80+0.5% CMC solution, and diluted to the corresponding concentration.

Experimental Method (1) The mice were subcutaneously inoculated with SU-DHL-4 cells (B cell lymphoma SU-DHL-4 cells were purchased from ATCC). When the tumors grown to 100-150 mm³, the animals were grouped according to the tumor volume (D0). The dose and regimen of the administration are shown in Table 6.

(2) Observation and recording: the tumor volume was measured 2 to 3 times per week, the mice were weighed, and the data were recorded.

(3) Tumor measurement and endpoint

The endpoint is mainly dependent on whether the tumor growth is delayed or whether the mouse is cured. The tumor volume (in mm³) was measured twice a week with caliper in two dimensions.

The tumor volume (V) is calculated as:

$$V = 0.5 \times a \times b^2,$$

wherein a and b represent length and width, respectively;

$$T/C\ (\%) = (T-T_0)/(C-C_0) \times 100,$$

wherein T and C represent the tumor volume at the end of the experiment; $T_0$ and $C_0$ represent the tumor volume at the beginning of the experiment. The T/C value (percentage) is indicative of anti-tumor efficacy.

Tumor growth inhibition rate (TGI) (%)=100−T/C (%);

When the tumor regressed, the tumor growth inhibition rate $$(TGI)\ (\%) = 100-(T-T_0)/T_0 \times 100$$

If the tumor volume is smaller than the initial volume, i.e. T<$T_0$ or C<$C_0$, it is defined as partial regression (PR); if the tumor completely disappears, it is defined as complete regression (CR).

(4) Data analysis: the statistics were summarized, including mean and standard error of mean (SEM), statistical analysis of differences in tumor volume between groups, and analysis of data obtained by drug interaction that was carried out at the optimal treatment time point after the last administration (Day 14 after grouping). One-way variance analysis was performed to compare tumor volume and tumor weight between groups. When a non-significant F-statistic was obtained (p<0.001, treatment variance vs. error variance), single-tailed Mann-Whitney statistical analysis was performed to compare tumor volumes of the two groups, and P<0.05 was considered as statistically significant.

Experimental Results

TABLE 6

Effect of the combined administration on the subcutaneous transplantation tumor in mice inoculated with the human B cell lymphoma SU-DHL-4 cells

| Groups | Administration | Route | Mean tumor volume (mm³) D 0 | SEM | Mean tumor volume (mm³) D 14 | SEM | % T/C D 14 | % tumor inhibition rate D 14 | | Partial regression | Complete regression | Number of animals in each group at the end of the experiment |
|---|---|---|---|---|---|---|---|---|---|---|---|---|
| Solvent | D 0-13 | PO, BID | 113.2 | 4.8 | 751.8 | ±146.7 | — | — | | 0 | 0 | 8 |
| Compound A 50 mg/kg | D 0-13 | PO, BID | 122.4 | 4.8 | 276.9 | ±73.5 | 24 | 76 | * | 1 | 1 | 8 |
| Compound B 50 mg/kg | D 0-13 | PO. BID | 126.6 | 5.3 | 384.7 | ±145.0 | 40 | 60 | * | 2 | 1 | 8 |
| Compound A 50 mg/kg + compound B 50 mg/kg | D 0-13 | PO, BID | 129.7 | 3.8 | 186.2 | ±66.0 | 9 | 91 | ** | 2 | 1 | 8 |

D 0: the time of the first administration;
PO: oral administration;
BID: twice a day;
* P < 0.05,
** P < 0.01, comparison with the solvent.

Experimental Conclusion

Figure 5:
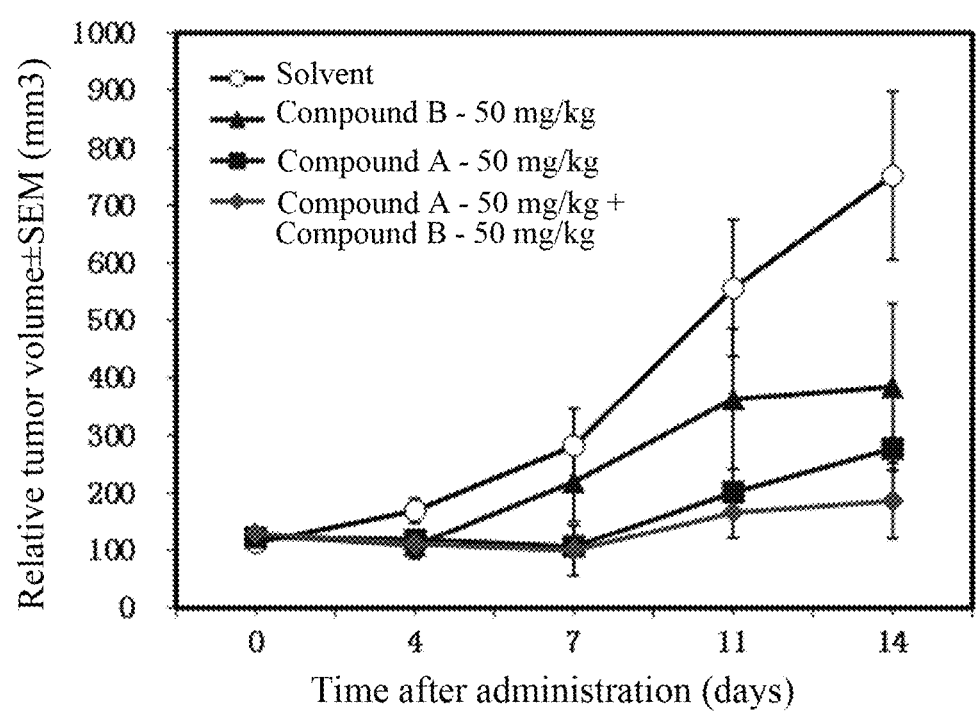
FIG. 5 shows the efficacy of the combined administration of an EZH2 inhibitor and a BTK inhibitor of the present invention (the combination of compound B and compound A) and the administration of single component (compound B, compound A) on the subcutaneous transplantation tumor in mice inoculated with B cell lymphoma SU-DHL-4 cells.

It can be seen from the data in Table 6 that compound A (50 mg/kg, PO, QD×14) inhibited the growth of the subcutaneous transplantation tumor in mice inoculated with SU-DHL-4 cells, and the tumor growth inhibition rate was 76%; the tumor partially regressed in 1/8 of mice, and the tumor completely regressed in 1/8 of mice. Compound B (50 mg/kg, PO, QD×14) had a tumor growth inhibition rate of 60% against SU-DHL-4 cells; the tumor partially regressed in 2/8 of mice, and the tumor completely regressed in 1/8 of mice. When compound A and compound B were administered in combination, the tumor growth inhibition rate was increased to 91%; the tumor partially regressed in 2/8 of mice, and the tumor completely regressed in 118 of mice; and the efficacy was significantly stronger than that of compound A or compound B alone (see FIG. 5). The combined administration of the two compounds significantly inhibited the growth of the subcutaneous transplantation tumor in mice inoculated with the human B cell lymphoma SU-DHL-4 cells, and induced partially or completely regression of the tumor. When the two compounds were administered in combination, the efficacy was improved, and the tumor-bearing mice had decreased body weight, but were resistant to the compounds.

In summary, the combined effect of the BTK inhibitor compound A and the EZH2 inhibitor compound B of the present invention is better than the effect of single compound, and such a combination has a synergistic effect.

What is claimed is:

1. A method for treating a tumor in a subject in need thereof, the method comprising administering to the subject a combination of an EZH2 inhibitor and a BTK inhibitor, wherein the EZH2 inhibitor is a compound of formula (I):

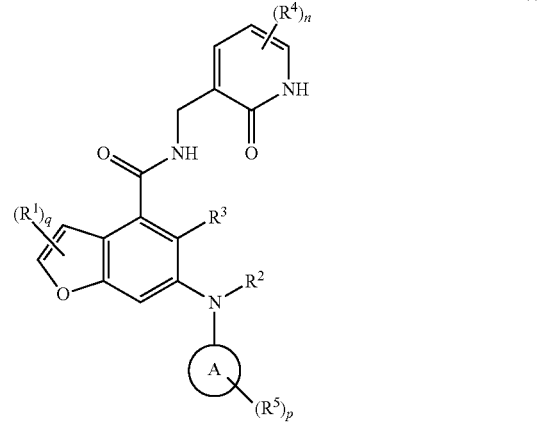

or a pharmaceutically acceptable salt thereof or a stereoisomer thereof,
wherein,
ring A is selected from the group consisting of heterocyclyl and cycloalkyl;
each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, $-OR^6$, $-C(O)R^6$, $-C(O)OR^6$, $-S(O)_mR^6$, $-S(O)_mNR^7R^8$ and $-(CH_2)_xR^a$, wherein the alkyl, haloalkyl, heterocyclyl, aryl and heteroaryl are each independently and optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —NR$^7$R$^8$, wherein the cycloalkyl and heterocyclyl are each independently and optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^2$ is hydrogen or alkyl, wherein the alkyl is optionally substituted by one or more substituents selected from the group consisting of halogen, hydroxy, cyano, cycloalkyl and heterocyclyl;

$R^3$ is selected from the group consisting of hydrogen, alkyl, halogen, cyano, alkoxy and haloalkyl;

each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —OR$^6$, —C(O)R$^6$, —C(O)OR$^6$, —S(O)$_m$R$^6$, —S(O)$_m$NR$^7$R$^8$ and —NR$^7$R$^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —OR$^6$, —C(O)R$^6$, —C(O)OR$^6$, —S(O)$_m$R$^6$, —S(O)$_m$NR$^7$R$^8$ and —NR$^7$R$^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;
n is 0, 1, 2 or 3;
p is 0, 1, 2, 3, 4 or 5;
q is 0, 1 or 2; and
x is 0, 1, 2 or 3.

2. The method according to claim 1, wherein the EZH2 inhibitor is a compound of formula (IA):

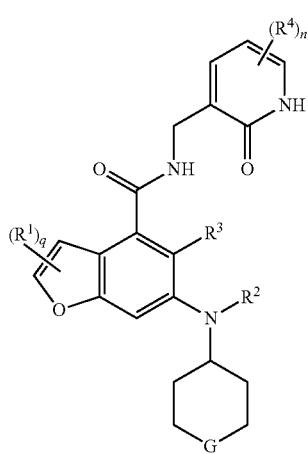

(IA)

or a pharmaceutically acceptable salt thereof or a stereoisomer thereof, wherein, G is selected from the group consisting of CR$^b$R$^c$, C═O, NR$^d$, S(O)$_m$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —OR$^6$, —C(O)R$^6$, —C(O)OR$^6$, —S(O)$_m$R$^6$ and —NR$^7$R$^8$;

$R^d$ is selected from the group consisting of hydrogen, alkyl, cycloalkyl, haloalkyl, hydroxyalkyl, heterocyclyl, aryl, heteroaryl, —C(O)R$^6$, —C(O)OR$^6$ and —S(O)$_m$R$^6$; and $R^1$ to $R^4$, $R^6$ to $R^8$, n, m and q are as defined in claim 1.

3. The method according to claim 1, wherein the EZH2 inhibitor is a compound of formula (TB):

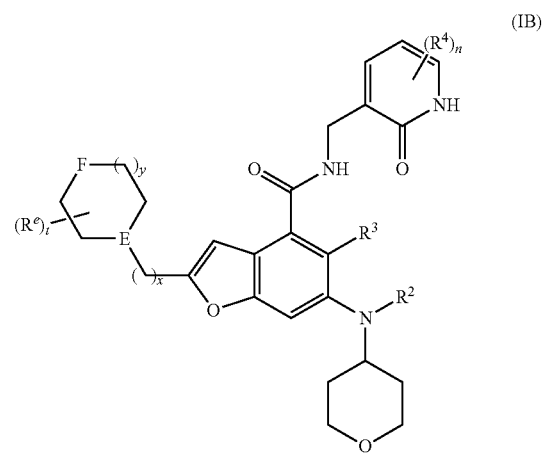

(IB)

or a pharmaceutically acceptable salt thereof or a stereoisomer thereof, wherein, E is CH or nitrogen;

F is selected from the group consisting of CR$^b$R$^c$, C═O, NR$^d$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —OR$^6$, —C(O)R$^6$, —C(O)OR$^6$, —S(O)$_m$R$^6$ and —NR$^7$R$^8$;

$R^d$ is selected from the group consisting of hydrogen, alkyl, cycloalkyl, haloalkyl, hydroxyalkyl, heterocyclyl, aryl, heteroaryl, —C(O)R$^6$, —C(O)OR$^6$ and —S(O)$_m$R$^6$;

each $R^e$ is identical or different and each is independently selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

t is 0, 1, 2, 3, 4 or 5;
x is 0, 1, 2 or 3;
y is 0, 1, 2 or 3; and
$R^2$ to $R^4$, $R^6$ to $R^8$, m and n are as defined in claim 1.

4. The method according to claim 1, wherein the EZH2 inhibitor is a compound of formula (IC):

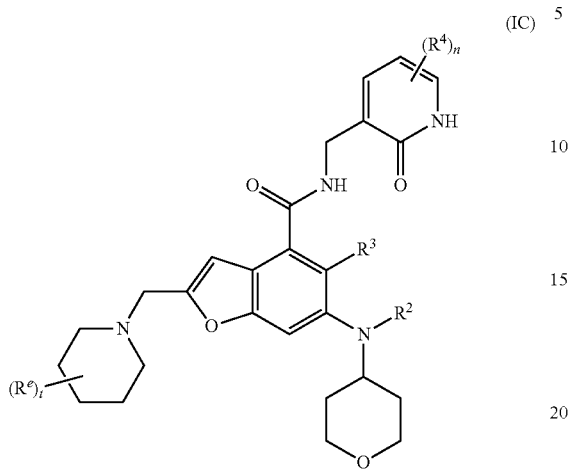

or a pharmaceutically acceptable salt thereof or a stereoisomer thereof,
wherein,
each $R^e$ is identical or different and is independently selected from the group consisting of hydrogen, alkyl and halogen;
t is 0, 1, 2, 3, 4 or 5; and
$R^2$ to $R^4$ and n are as defined in claim 1.

5. The method according to claim 1, wherein the EZH2 inhibitor is a compound of formula (ID):

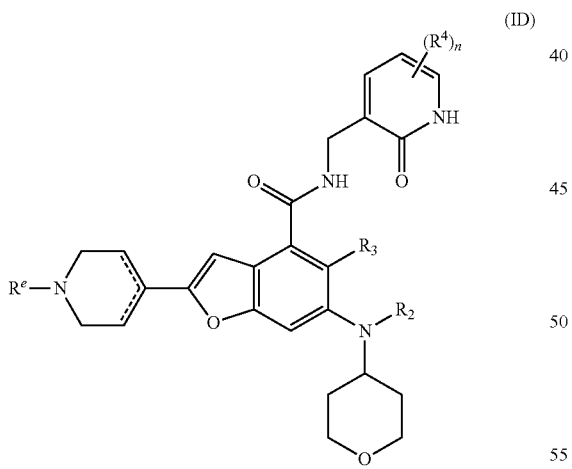

or a pharmaceutically acceptable salt thereof or a stereoisomer thereof,
wherein,
$R^e$ is selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl; and
$R^2$ to $R^4$ and n are as defined in claim 1.

6. The method according to claim 1, wherein the BTK inhibitor is a compound of formula (II):

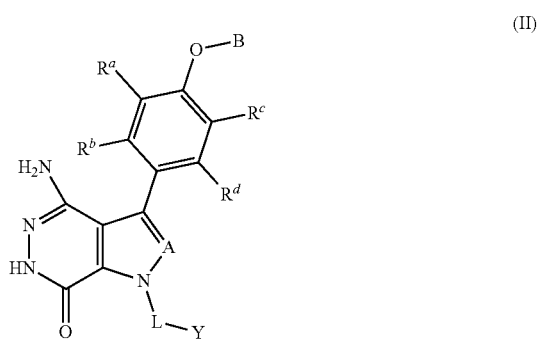

or a pharmaceutically acceptable salt or a stereoisomer thereof,
wherein,
A is selected from the group consisting of $CR^1$ and N;
$R^1$ is selected from the group consisting of hydrogen, halogen and optionally substituted alkyl, wherein the substituent is selected from the group consisting of halogen, hydroxy, cyano, nitro, carboxy, amino, alkyl, alkoxy and haloalkyl;
$R^a$, $R^b$, $R^c$ and $R^d$ are each independently selected from the group consisting of hydrogen, halogen, hydroxy, cyano, nitro, optionally substituted alkyl and optionally substituted alkoxy, wherein the substituent is selected from the group consisting of halogen, hydroxy, cyano, nitro, carboxy, amino, alkyl, alkoxy and haloalkyl;
B is selected from the group consisting of hydrogen, optionally substituted cycloalkyl, optionally substituted heterocyclyl, optionally substituted aryl and optionally substituted heteroaryl, wherein the substituent is selected from the group consisting of halogen, hydroxy, cyano, nitro, carboxy, amino, alkyl, alkoxy and haloalkyl;
L is selected from the group consisting of a bond and optionally substituted alkyl; and
Y is selected from the group consisting of optionally substituted cycloalkyl, optionally substituted heterocyclyl, optionally substituted aryl and optionally substituted heteroaryl, wherein the substituent is selected from the group consisting of halogen, hydroxy, cyano, nitro, carboxy, amino, alkyl, alkylcarbonyl, alkynylcarbonyl and haloalkyl.

7. A method for treating a tumor in a subject in need thereof, the method comprising administering to the subject a combination of an EZH2 inhibitor and a BTK inhibitor, wherein the EZH2 inhibitor is a compound of formula (IE):

(IE)

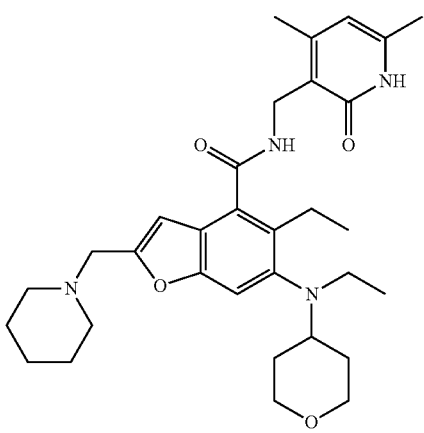

or a pharmaceutically acceptable salt thereof or a stereoisomer thereof, and
the BTK inhibitor is a compound of formula (IIA):

(IIA)

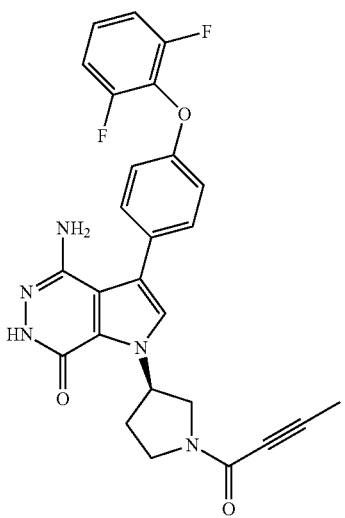

or a pharmaceutically acceptable salt thereof or a stereoisomer thereof.

8. The method according to claim 5, wherein the pharmaceutically acceptable salt is selected from the group consisting of phosphate, hydrochloride, methanesulfonate, maleate, malate, p-toluenesulfonate and besylate.

9. The method according to claim 1, wherein the BTK inhibitor is selected from the group consisting of Ibrutinib, Acalabrutinib, MSC-2364447, Spebrutinib, HM-71224, Plevitrexed, GS-4059, GDC-0853, SNS-062, CGP-53716, Idoxifene, BTG-511, Banoxantrone, Glucarpidase, Antidigoxin polyclonal antibody, Crotalidae polyvalent immune Fab (ovine, BTG) and Otelixizumab.

10. The method according to claim 1, wherein the combination optionally comprises a third component selected from the group consisting of an HDAC inhibitor, CDK4/6 inhibitor, ALK inhibitor, JAK2 inhibitor, Bcl-2 inhibitor, Hsp90 inhibitor, glucocorticoid, vinca alkaloid, antimetabolite, DNA damaging agent, Lenalidomide, Rituximab, PKC perturbagen, Lyn/Fyn inhibitor, Syk inhibitor, PI3K inhibitor, PKCβ inhibitor, IKK inhibitor, 20s proteasome, IRF-4, IRAK4 antibody, CXCR4 antibody, CXCR5 antibody, GLS antibody, PLK antibody, CD20 antibody, Topo II inhibitor, DNA methyltransferase inhibitor, Ras/MAPK inhibitor and FGFR1 inhibitor.

11. The method according to claim 10, wherein the HDAC inhibitor is selected from the group consisting of Panobinostat Lactate, Belinostat, Chidamide, Romidepsin, Vorinostat, Bexanostat and Entinostat; the CDK4/6 inhibitor is selected from the group consisting of Palbociclib, Blinatumomab, Tiagabine Hydrochloride and Itolizumab; the Bcl-2 inhibitor is selected from the group consisting of Venetoclax, Oblimersen Sodium, ABT-737 and HA14-1; the Hsp90 inhibitor is selected from the group consisting of Sebelipase alfa and Retaspimycin Hydrochloride; the JAK2 inhibitor is selected from the group consisting of Tofacitinib citrate, Ruxolitinib Phosphate, Lestaurtinib, Momelotinib Dihydrochloride, Peficitinib and Filgotinib; the PKC perturbagen is selected from the group consisting of Teprenone, Truheal, HO/03/03, Sotrastaurin, Enzastaurin and GF109203X; the ALK inhibitor is selected from the group consisting of Alectinib hydrochloride, Ceritinib, Crizotinib, Bendamustine, Carmustine, Lumostine, chlormethine hydrochloride and NVP-TAE684; the PI3K inhibitor is selected from the group consisting of GS-1101, IPI-145, BKM120, BEZ235, GDC-0941, AMG319, CAL-101 and A66; and the IKK inhibitor is selected from the group consisting of Auranofin, BAY 86-9766 and RDEA-119.

12. The method according to claim 10, wherein the tumor is lymphoma.

13. The method according to claim 12, wherein the lymphoma is non-Hodgkin lymphoma.

14. The method according to claim 13, wherein the non-Hodgkin lymphoma is B cell proliferative disease.

15. The method according to claim 14, wherein the B cell proliferative disease is selected from the group consisting of diffuse large B-cell lymphoma (DLBCL), chronic lymphocytic leukemia (CLL), small lymphocytic lymphoma (SLL), high-risk CLL or non-CLL/SLL lymphoma, follicular lymphoma (FL), mantle cell lymphoma (MCL), precursor B cell tumor, precursor B lymphoblastic leukemia (or lymphoma), mature (peripheral) B cell tumor, lymphoplasmacytic lymphoma (or immunoblastoma), extranodal mucosa-associated lymphoma, hairy cell leukemia, plasmacytoma (or plasma cell myeloma), Waldenstrom's macroglobulinemia, multiple myeloma, marginal zone lymphoma, Burkitt's lymphoma (BL), non-Burkitt high grade B cell lymphoma or extranodal marginal zone B cell lymphoma, acute or chronic myelogenous (or myeloid) leukemia, myelodysplastic syndrome and acute lymphoblastic leukemia.

16. The method according to claim 12, wherein a ratio of the EZH2 inhibitor to the BTK inhibitor is 0.001-1000.

17. The method according to claim 16, wherein the ratio of the EZH2 inhibitor to the BTK inhibitor is 0.1-10.

18. The method according to claim 17, wherein an administration dose of the EZH2 inhibitor is 1-2000 mg, and an administration dose of the BTK inhibitor is 1-1000 mg.

19. A pharmaceutical composition comprising an EZH2 inhibitor, a BTK inhibitor, and one or more pharmaceutically acceptable excipients, diluents or carriers, wherein the EZH2 inhibitor is a compound of formula (I):

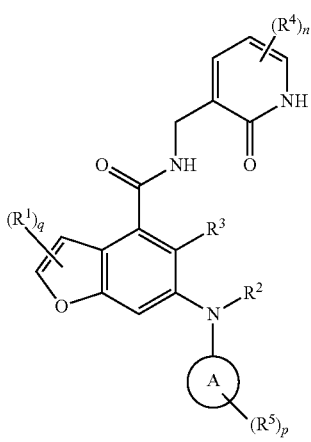

(I)

or a pharmaceutically acceptable salt thereof or a stereoisomer thereof,
wherein,
ring A is selected from the group consisting of heterocyclyl and cycloalkyl;
each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, $-OR^6$, $-C(O)R^6$, $-C(O)OR^6$, $-S(O)_mR^6$, $-S(O)_mNR^7R^8$ and $-(CH_2)_xR^a$, wherein the alkyl, haloalkyl, heterocyclyl, aryl and heteroaryl are each independently and optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
$R^a$ is selected from the group consisting of halogen, cycloalkyl, heterocyclyl and $-NR^7R^8$, wherein the cycloalkyl and heterocyclyl are each independently and optionally substituted by one or more substituents selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;
$R^2$ is hydrogen or alkyl, wherein the alkyl is optionally substituted by one or more substituents selected from the group consisting of halogen, hydroxy, cyano, cycloalkyl and heterocyclyl;
$R^3$ is selected from the group consisting of hydrogen, alkyl, halogen, cyano, alkoxy and haloalkyl;
each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, $-OR^6$, $-C(O)R^6$, $-C(O)OR^6$, $-S(O)_mR^6$, $-S(O)_mNR^7R^8$ and $-NR^7R^8$;
each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, $-OR^6$, $-C(O)R^6$, $-C(O)OR^6$, $-S(O)_mR^6$, $-S(O)_mNR^7R^8$ and $-NR^7R^8$;
$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more substituents selected from the group consisting of alkyl, halogen, hydroxy, amino, alkoxycarbonyl, nitro, cyano, alkoxy, hydroxyalkyl, cycloalkyl, heterocyclyl, aryl and heteroaryl;
m is 0, 1 or 2;
n is 0, 1, 2 or 3;
p is 0, 1, 2, 3, 4 or 5;
q is 0, 1 or 2; and
x is 0, 1, 2 or 3.

20. The pharmaceutical composition according to claim 19, wherein the BTK inhibitor is a compound of formula (II):

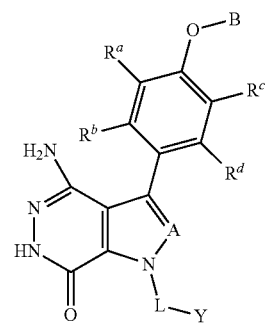

(II)

or a pharmaceutically acceptable salt thereof or a stereoisomer thereof,
wherein,
A is selected from the group consisting of $CR^1$ and N;
$R^1$ is selected from the group consisting of hydrogen, halogen and optionally substituted alkyl, wherein the substituent is selected from the group consisting of halogen, hydroxy, cyano, nitro, carboxy, amino, alkyl, alkoxy and haloalkyl;
$R^a$, $R^b$, $R^c$ and $R^d$ are each independently selected from the group consisting of hydrogen, halogen, hydroxy, cyano, nitro, optionally substituted alkyl and optionally substituted alkoxy, wherein the substituent is selected from the group consisting of halogen, hydroxy, cyano, nitro, carboxy, amino, alkyl, alkoxy and haloalkyl;
B is selected from the group consisting of hydrogen, optionally substituted cycloalkyl, optionally substituted heterocyclyl, optionally substituted aryl and optionally substituted heteroaryl, wherein the substituent is selected from the group consisting of halogen, hydroxy, cyano, nitro, carboxy, amino, alkyl, alkoxy and haloalkyl;
L is selected from the group consisting of a bond and optionally substituted alkyl; and
Y is selected from the group consisting of optionally substituted cycloalkyl, optionally substituted heterocyclyl, optionally substituted aryl and optionally substituted heteroaryl, wherein the substituent is selected from the group consisting of halogen, hydroxy, cyano, nitro, carboxy, amino, alkyl, alkylcarbonyl, alkynylcarbonyl and haloalkyl.

* * * * *